(12) United States Patent
Park et al.

(10) Patent No.: US 9,321,031 B2
(45) Date of Patent: Apr. 26, 2016

(54) MAGNETIC-CORED DENDRIMER, THE METHOD FOR PREPARING THE SAME, AND THE CONTAMINANT TREATMENT METHOD USING THE SAME

(71) Applicant: IUCF-HYU (Industry-University Cooperation Foundation Hanyang University), Seoul (KR)

(72) Inventors: Jae-Woo Park, Seoul (KR); Jun-Won Jang, Seoul (KR); Han-Uk Lee, Pocheon-si (KR)

(73) Assignee: IUCF-HYU (INDUSTRY-UNIVERSITY COOPERATION FOUNDATION HANYANG UNIVERSITY) (KR)

( * ) Notice: Subject to any disclaimer, the term of this patent is extended or adjusted under 35 U.S.C. 154(b) by 260 days.

(21) Appl. No.: 13/926,143

(22) Filed: Jun. 25, 2013

(65) Prior Publication Data

US 2013/0289292 A1   Oct. 31, 2013

Related U.S. Application Data

(62) Division of application No. 12/856,823, filed on Aug. 16, 2010, now abandoned.

(30) Foreign Application Priority Data

Feb. 11, 2010  (KR) .................. 10-2010-0013057
Jul. 6, 2010   (KR) .................. 10-2010-0064795

(51) Int. Cl.
   *C07C 233/91*   (2006.01)
   *C07C 211/09*   (2006.01)
   (Continued)

(52) U.S. Cl.
   CPC .............. *B01J 20/223* (2013.01); *B82Y 40/00* (2013.01); *C01G 49/02* (2013.01); *C01G 49/04* (2013.01);
   (Continued)

(58) Field of Classification Search
   None
   See application file for complete search history.

(56) References Cited

U.S. PATENT DOCUMENTS 8,834,618 B2 *  9/2014  Baran et al. ................. 106/2

OTHER PUBLICATIONS

Gao et al., "Study of streptavidin coated onto PAMAM dendrimer modified magnetite nanoparticles." J. Magnetism and Magnetic Materials 293 (2005), pp. 48-54. Available online as of Mar. 2, 2005.*

(Continued)

*Primary Examiner* — Stuart Hendrickson
*Assistant Examiner* — Daniel Berns
(74) *Attorney, Agent, or Firm* — Cantor Colburn LLP

(57) ABSTRACT

Provided is a magnetic-cored dendrimer represented by the following Chemical Formula (1):

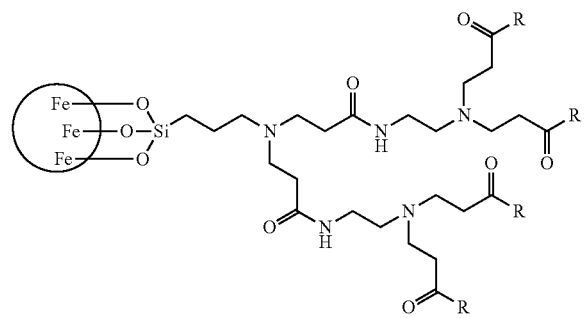

(1)

wherein R represents a functional group represented by the following Chemical Formula (2) or (3):

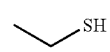

(2)

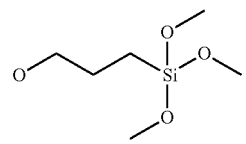

(3)

1 Claim, 25 Drawing Sheets

(51) Int. Cl.
  C07C 211/65  (2006.01)
  B01J 20/26   (2006.01)
  B01J 20/22   (2006.01)
  C01G 49/08   (2006.01)
  H01B 1/08    (2006.01)
  C01G 49/02   (2006.01)
  C01G 49/06   (2006.01)
  H01B 1/02    (2006.01)
  H01B 1/12    (2006.01)
  C01G 49/04   (2006.01)
  B82Y 40/00   (2011.01)
  C07F 7/18    (2006.01)
  C02F 1/28    (2006.01)
  C02F 1/48    (2006.01)
  C02F 1/66    (2006.01)
  C02F 101/20  (2006.01)

(52) U.S. Cl.
  CPC ............... *C01G 49/06* (2013.01); *C01G 49/08* (2013.01); *C02F 1/288* (2013.01); *C07F 7/1836* (2013.01); *H01B 1/02* (2013.01); *H01B 1/08* (2013.01); *H01B 1/12* (2013.01); *C02F 1/285* (2013.01); *C02F 1/488* (2013.01); *C02F 1/66* (2013.01); *C02F 2101/20* (2013.01); *C02F 2303/16* (2013.01); *C02F 2305/08* (2013.01); *C07B 2200/11* (2013.01)

(56) References Cited

OTHER PUBLICATIONS

"Faculty—School of Mechanical Engineering, Shanghai Jiao Tong University: bio page of Dr. Feng Gao." (c)2009-2010. Viewed Jun. 24, 2015 at http://me.sjtu.edu.cn/english/faculty/showDetail.aspx?id=36.*

Garel et al., "Mechanism of Hydrolysis and Aminolysis of Homocysteine Thiolactone." Chem. Eur. J. 2006, vol. 12, pp. 4144-4152 (published online on Feb. 2, 2006).*

Jun Won Jang et al., "Surface molecule-controllable magnetic-dendrimer for environmental applications," The 238th ACS National Meeting, Washington, DC, Aug. 16-20, 2009.

Han Uk Lee et al., "Interaction between lower generation poly (amidoamine), dendrimers, and cadmium-contaminated soils," The 238th ACS National Meeting, Washington, DC, Aug. 16-20, 2009.

* cited by examiner (a)  (b)

(a)  (b)

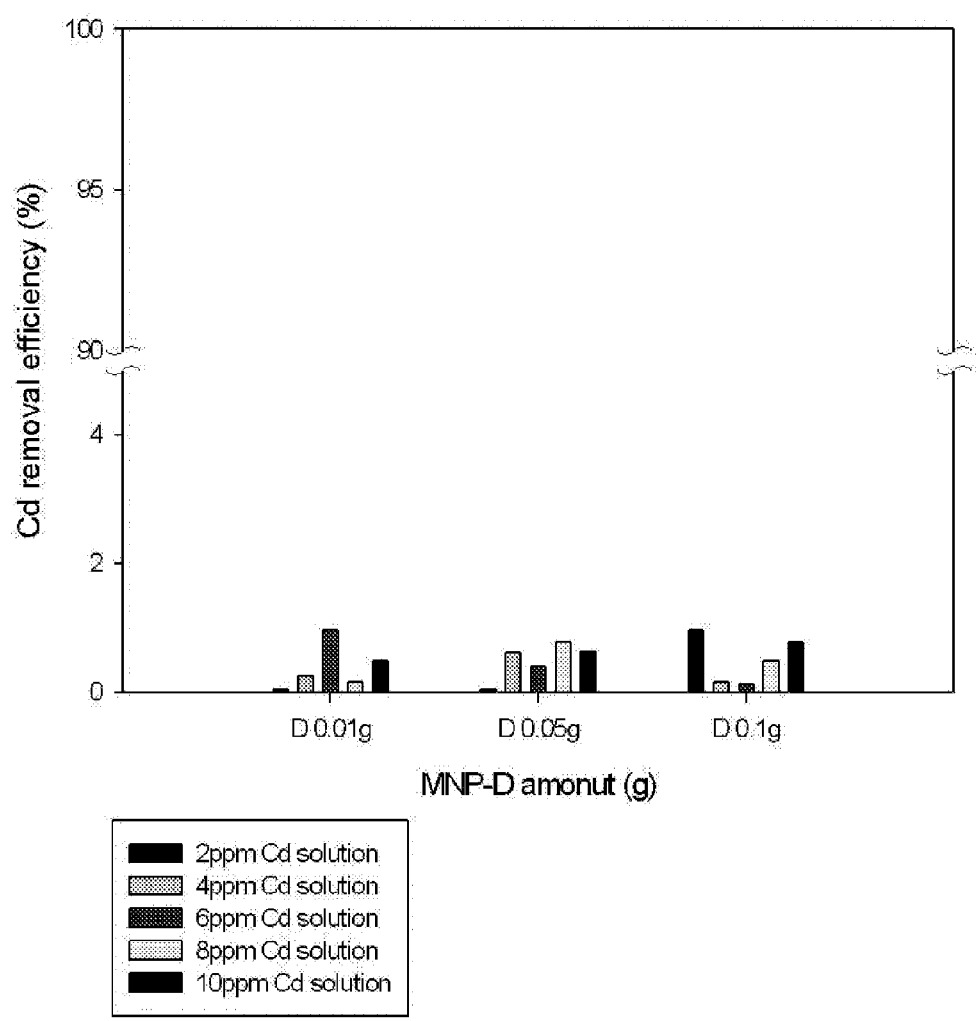

(a)

(b)

MAGNETIC-CORED DENDRIMER, THE METHOD FOR PREPARING THE SAME, AND THE CONTAMINANT TREATMENT METHOD USING THE SAME

CROSS-REFERENCE TO RELATED APPLICATIONS

This application is a divisional of U.S. application Ser. No. 12/856,823, filed on Aug. 16, 2010, which claims priority under 35 U.S.C. §119 to Korean Patent Applications No. 10-2010-0013057, filed on Feb. 11, 2010 and No. 10-2010-0064795, filed on July 6, in the Korean Intellectual Property Office, the disclosures of which are incorporated herein by reference in its entirety.

TECHNICAL FIELD

The following disclosure relates to a magnetic-cored dendrimer, and in particular, to a magnetic-cored dendrimer end-capped with hydrophilic or hydrophobic terminal groups. The following disclosure also relates to a method for preparing the magnetic-cored dendrimer and a method for adsorbing and separating contaminants using the same.

BACKGROUND

The term 'dendrimer' is derived from 'dendro' (meaning tree-like in Greek)+polymer, and refers to an oligomer or polymer having a large number of branches arranged in a regular structure as the name suggests. Dendrimers are also called "arborols" meaning tree in Latin) or cascade polymers. The dendrimers have a polydispersity of about 1, an approximately spherical shape, and a large number of functional groups in the outermost portions thereof, and thus show unique chemical and physical properties.

Due to such unique properties, dendrimers have been spotlighted as ideal materials in various industrial fields. Typical examples of such industrial fields include additives, powder coatings, blend materials, delivery devices, liquid crystals, functional carriers, catalysts, sensors, multi-functional crosslinking agents, etc.

More recently, application of dendrimers to medical and pharmaceutical fields has drawing attentions. In this context, dendrimers may be provided in various forms having a wide variety of applicability, like carbon nanotubes (CNT). In addition, as shown in FIG. 2, dendrimers may be applied in various forms, and thus are known to be superior to nanotubes or fullerenes.

As revealed by search of reference publications or DECHEMA data, approximately 200 institutes or researchers are conducting studies on the dendrimers. For example, their studies may be classified into the following three categories: Voegtle's model [polyamidoamine (PAMAM) dendrimers], Frechet's model (ether-bonded dendrimers) and Tomalia's model (ester-bonded dendrimers). The dendrimers have been commercially available as electric/electronic materials, catalysts, etc. More recently, carbosilane dendrimers suggested by van der Made are being studied.

Although dendrimers have been studied actively as mentioned above, studies thereof for environmental application are still in early stage. Mamadou Diallo of the California Institute of Technology has studied about treatment of anionic perchlorate with poly(amidoamine) (PAMAM) dendrimers and treatment of heavy metals, such as copper, using a dendrimer-membrane. And, Yinhui Xu of Auburn University has developed a method for treating copper and lead with a dendrimer from contaminated soil.

However, most of the studies are merely in the early stage for environmental application of previously commercialized dendrimers. Moreover, such previous studies use filtration of the treated dendrimers with a membrane, and thus are not cost-efficient. In Korea, there is no study about application of dendrimers in the field of environmental industry, and studies of dendrimers are limited mainly to some industrial fields, such as adjuvants for medical or biochemical products, display materials, or electric/electronic devices.

Meanwhile, in the iron and steel industry and manufacturing industry, industrial water has been treated to remove various types of contaminants incorporated during the processes. The contaminants are removed from industrial wastewater by using a process including agglomeration, precipitation or filtration. Such an agglomeration/precipitation process treats industrial wastewater by converting the contaminants into crude floccules with a coagulant and an agglomerating agent and by carrying out solid/liquid separation in a precipitation unit. However, because the resultant contaminant floccules show a low precipitation rate in the precipitate unit, a large-scale precipitation unit is required to collect the agglomerated floccules. Therefore, such a process has a disadvantage in that it requires high investment costs for the equipment and site to build a plant. In addition, some chemicals used in the agglomeration/precipitation process may cause secondary environmental pollution, and the precipitation sludge is not amenable to recycling. As a result, there is another disadvantage in that the collected contaminants and the agglomerating agent are discarded together.

According to the related art, an apparatus for collecting magnetic contaminants using magnetic power was developed to remove the magnetic contaminants floating on wastewater, such as one discharged from the iron making industry. However, in the case of wastewater from the iron making industry, the magnetic contaminants may have insufficient magnetic properties, particularly when they have a small particle diameter or low magnetizing capability. In this case, it is difficult to remove the contaminants with such a conventional magnetic separation system. Due to this, it is required that the contaminants are passed through the magnetic separation system several times. Therefore, when purifying wastewater containing magnetic nanoparticles, a complicated process is required, and a large area of land is necessary to build the processing systems, thereby resulting in marked limitation in the place where the process is carried out.

SUMMARY

An embodiment of the present disclosure is directed to providing a novel magnetic-cored dendrimer end-capped with hydrophilic or hydrophobic molecules capable of adsorbing contaminants, such as heavy metals.

Another embodiment of the present disclosure is directed to providing a method for preparing a magnetic-cored dendrimer end-capped with hydrophilic or hydrophobic molecules.

Still another embodiment of the present disclosure is directed to providing a method for separating contaminants using a magnetic-cored dendrimer end-capped with hydrophilic or hydrophobic molecules.

Still another embodiment of the present disclosure is directed to providing an apparatus for treating magnetic nanoparticles, which performs agitation of wastewater containing magnetic nanoparticles simultaneously with wastewater treatment.

Yet another embodiment of the present disclosure is directed to providing an apparatus for treating magnetic nanoparticles, which performs agitation of wastewater containing magnetic nanoparticles simultaneously with wastewater treatment by driving a propeller with an electromagnet in an agitator.

In one general aspect, there is provided a magnetic-cored dendrimer represented by the following Chemical Formula (1):

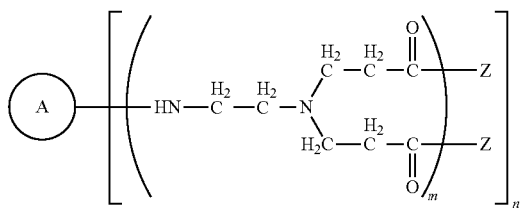

(1)

wherein A represents a metal nanoparticle; Z is a hydrophilic functional group or hydrophobic functional group; and m and n each represent an integer 1 or larger. Particularly, m may be an integer of 1 to 5.

According to a particular embodiment, the metal nanoparticle A may be an iron nanoparticle having a crystal form of magnetite ($Fe_3O_4$) or maghemite ($\gamma$-$Fe_2O_3$).

According to an embodiment, Z may be a hydrophilic functional group selected from the group consisting of —$NH_2$, —OH, —COOH and —SH, or a hydrophobic functional group, such as —$C_6H_6$ or —$CH_3$.

According to another embodiment, the magnetic-cored dendrimer disclosed herein may be any one selected from the following Chemical Formulae (2) to (4):

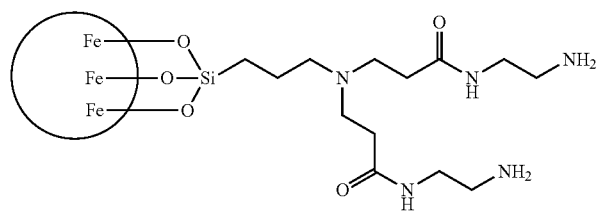

(2)

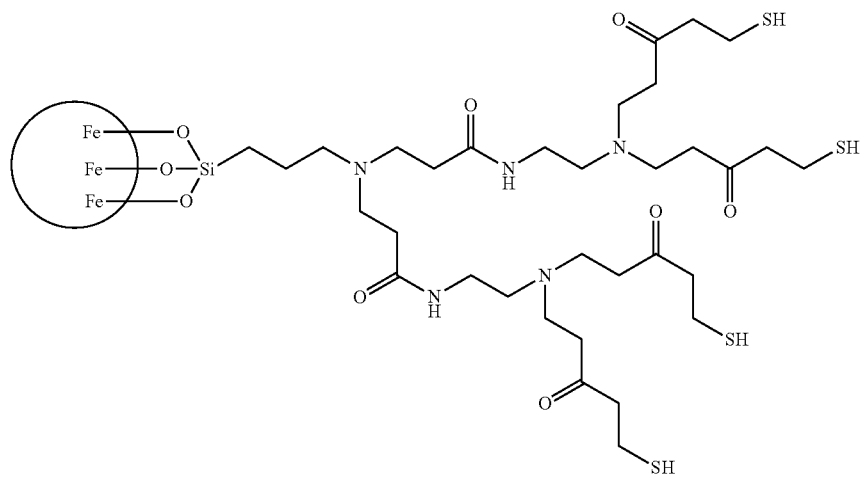

(3)

(4)
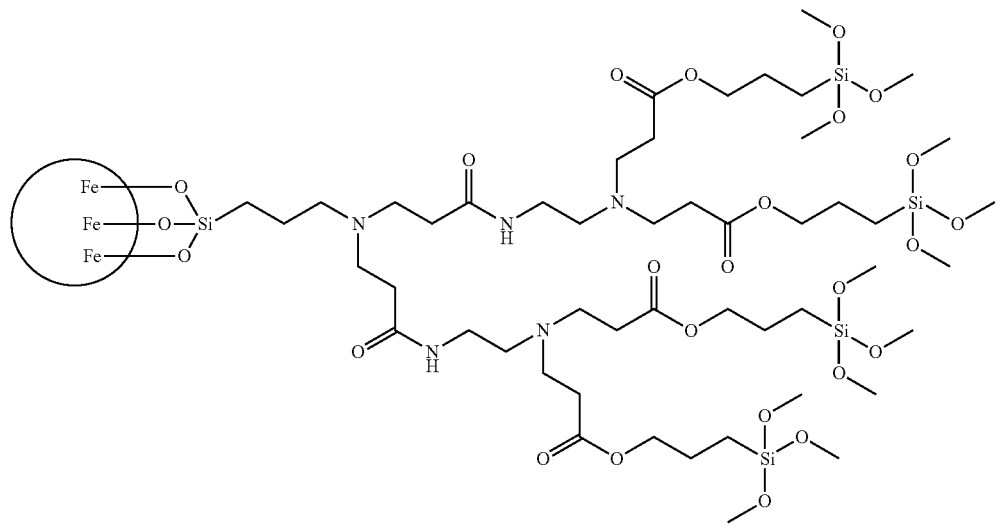
In another general aspect, there is provided a method for preparing a magnetic-cored dendrimer represented by any one of Chemical Formulae (2) to (4) through the following Reaction Schemes 1 to 3:
[Reaction Scheme 1]
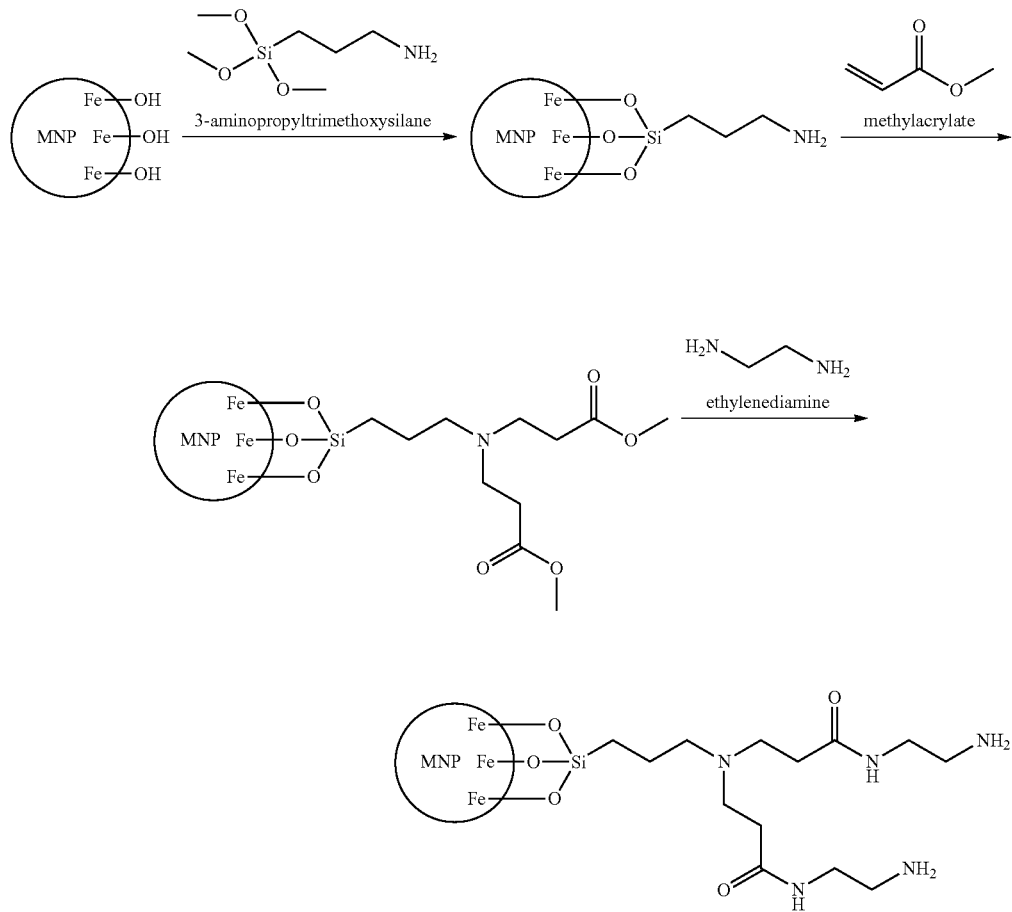

[Reaction Scheme 2]
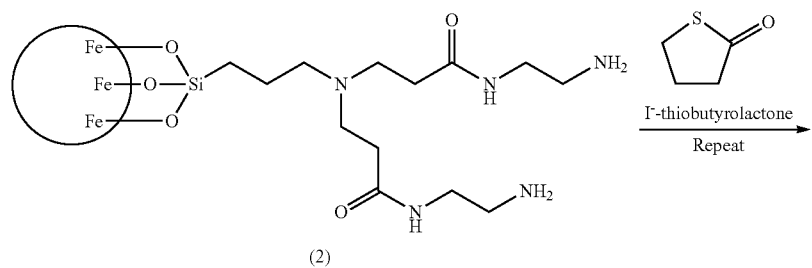
(2)
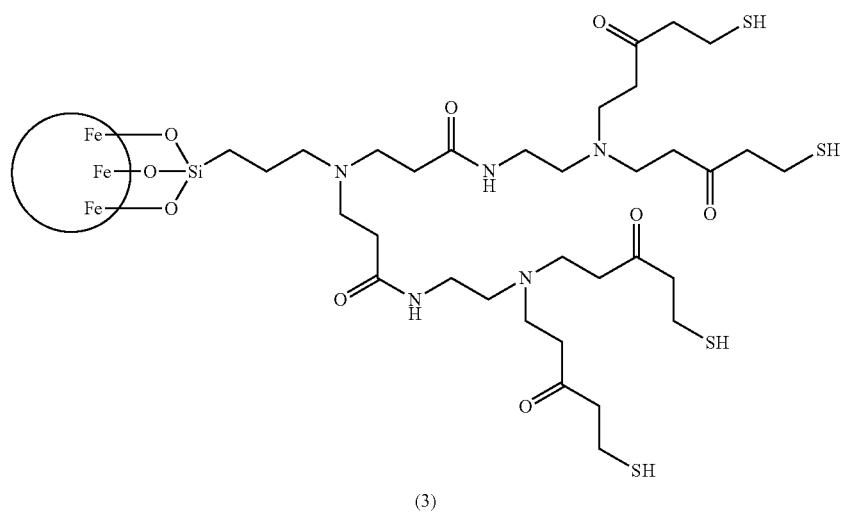
(3)
[Reaction Scheme 3]
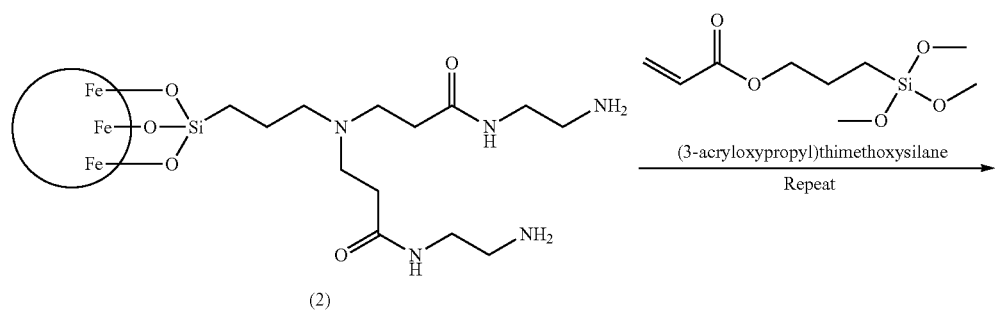
(2)

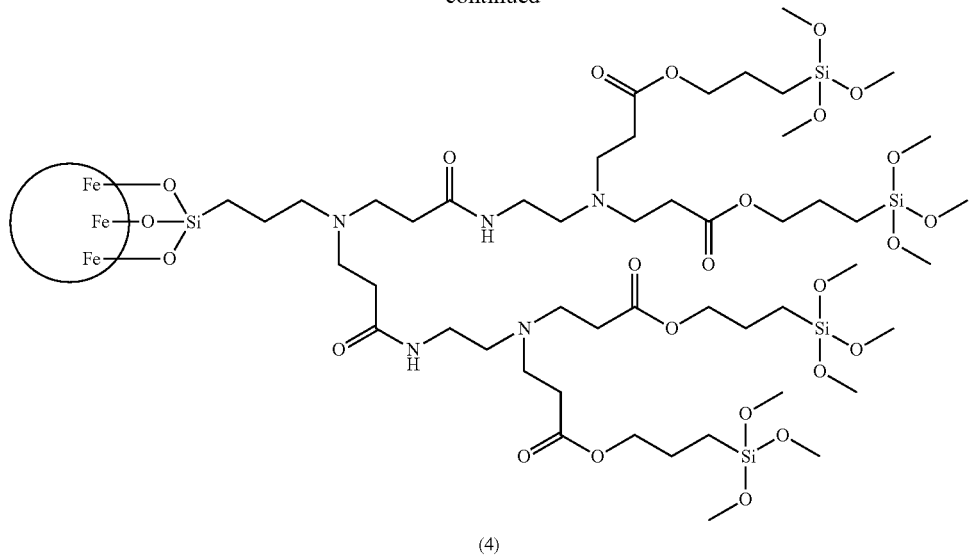

(4)

In still another general aspect, there is provided a method for separating hydrophilic or hydrophobic contaminants using the magnetic-cored dendrimer represented by the above Chemical Formula (1), the method including: allowing the contaminants to be adsorbed on the magnetic-cored dendrimer; and separating the dendrimer having the contaminants adsorbed thereon by using a magnet.

Particularly, the contaminants that may be separated by the dendrimer include both hydrophilic and hydrophobic contaminants. For example, the contaminants may be heavy metals. The method is particularly useful for the separation of cadmium, which may be carried out more effectively in a solution of pH of 4 or higher. In addition, since cadmium is desorbed from the dendrimer at a pH 4 or lower, the dendrimer may be reutilized based on this.

In still another general aspect, there is provided an apparatus for recovering magnetic nanoparticles, including: a wastewater tank having a main body to which wastewater containing magnetic nanoparticles is introduced, and a cover disposed on the top of the main body; a plurality of magnetic bars attached to the cover to generate magnetic power; an adsorbent storage tank from which magnetic fine powder capable of adsorbing the magnetic nanoparticles is supplied to the wastewater tank; and an agitator provided in the wastewater tank to carry out agitation of the wastewater and the magnetic fine powder.

According to a particular embodiment, the agitator may be rotated at a speed between 100 rpm and 300 rpm.

In yet another general aspect, there is provided an apparatus for recovering magnetic nanoparticles, including: a wastewater tank having a main body to which wastewater containing magnetic nanoparticles is introduced, and a cover disposed on the top of the main body; a hollow tubular magnetic bar attached to the cover to generate magnetic power; an adsorbent storage tank from which magnetic fine powder capable of adsorbing the magnetic nanoparticles is supplied to the wastewater tank; and an agitator penetrating through and disposed in the inner part of the magnetic bar, including a rotatable body driven by the magnetic bar and a propeller attached to the end of the rotatable body, and carrying out agitation of the wastewater and the magnetic fine powder.

According to a particular embodiment, a plurality of magnetic bars may be provided in the wastewater tank at regular intervals.

According to an embodiment, the apparatus may further include a load control unit applying frictional force to the rotatable body.

According to an embodiment, the magnetic fine powder may be a magnetic-cored dendrimer represented by the following Chemical Formula (1):

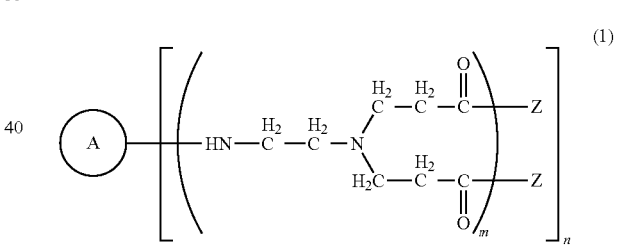

wherein A represents a metal nanoparticle; Z is a hydrophilic functional group or hydrophobic functional group; and m and n each represent an integer 1 or larger.

According to a particular embodiment, m may be an integer of 1 to 5.

According to an embodiment, the metal nanoparticle A may be an iron nanoparticle having a crystal form of magnetite ($Fe_3O_4$) or maghemite ($\gamma$-$Fe_2O_3$).

According to an embodiment, Z may be a hydrophilic functional group selected from the group consisting of —$NH_2$, —OH, —COOH and —SH.

According to an embodiment, Z may be a hydrophobic functional group, such as —$C_6H_6$ or —$CH_3$.

The magnetic-cored dendrimer disclosed herein has various types of surface terminal groups, and thus may adsorb and remove hydrophilic or hydrophobic contaminants as well as heavy metals. Therefore, the magnetic-cored dendrimer may be used as an adsorbent for hydrophilic or hydrophobic contaminants, a chelating agent for recovering heavy metals and noble metals, or the like. The magnetic-cored dendrimer may also be applied to a wide variety of wastewater treatment facilities, soil contaminant treatment facilities, nuclear waste disposal facilities, leachate treatment in a waste disposal site, mines, or the like. In addition, used magnetic-cored dendrimers may be recovered through a simple magnetic separation system using a magnet instead of an expensive membrane system, and the recovered dendrimers may be regenerated by ion exchange or acid treatment, resulting in excellent cost efficiency. Further, the dendrimer disclosed herein is not toxic itself but is a biochemically degradable eco-friendly green material.

In addition, the apparatus disclosed herein includes an agitator and a magnetic bar, both of which are provided in a wastewater tank, so that agitation of wastewater may be performed simultaneously with water purification. Therefore, it is possible to reduce the processing time required for purifying industrial water, such as one from the iron making industry. Further, the apparatus for recovering magnetic nanoparticles has an agitation system formed integrally with a water purification system, and thus may be installed in a minimized space. Therefore, the apparatus for recovering magnetic nanoparticles may be installed in a desired place with no particular limitation, and the recovered nanoparticles and the magnetic fine powder may be reutilized.

Other features and aspects will be apparent from the following detailed description, the drawings, and the claims.

BRIEF DESCRIPTION OF THE DRAWINGS

The above and other objects, features and advantages of the present disclosure will become apparent from the following description of certain exemplary embodiments given in conjunction with the accompanying drawings, in which:

FIGS. 9A to 9C are graphs each showing the removal of Cd using the magnetic-cored dendrimer MNP-D (G=2) under pH 3 (FIG. 9A), pH 6 (FIG. 9B) and pH 11 (FIG. 9C);

DETAILED DESCRIPTION OF EMBODIMENTS

Figure 1:
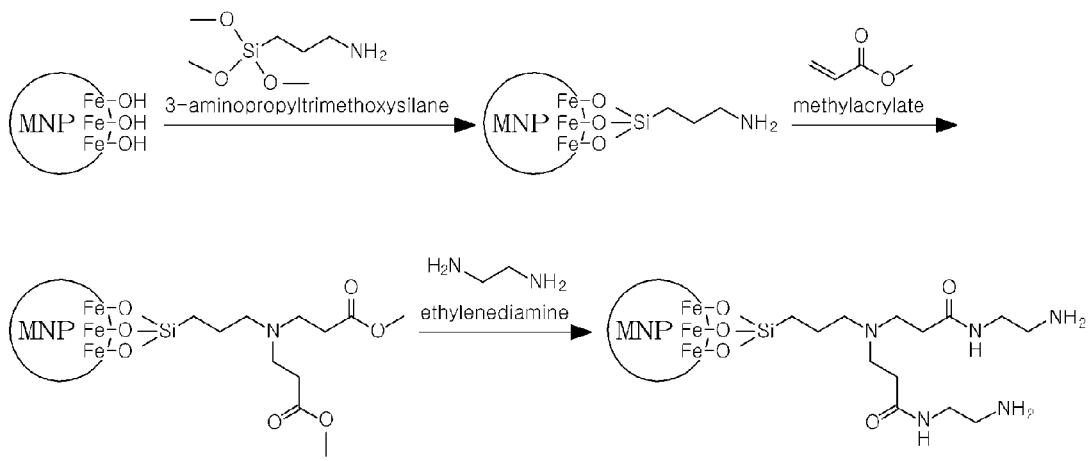
FIG. 1 is a schematic view showing the preparation of a magnetic-cored dendrimer end-capped with $NH_2$ groups.

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

The magnetic-cored dendrimer disclosed herein is represented by the following Chemical Formula (1):

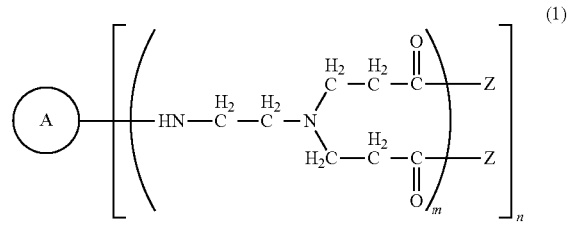

wherein A represents a metal nanoparticle; Z is a hydrophilic functional group or hydrophobic functional group; and m and n each represent an integer 1 or larger. Particularly, m may be an integer of 1 to 5.

According to a particular embodiment, the metal nanoparticle A may be an iron nanoparticle having a crystal form of magnetite ($Fe_3O_4$) or maghemite ($\gamma$-$Fe_2O_3$).

According to an embodiment, Z may be a hydrophilic functional group selected from the group consisting of —$NH_2$, —OH, —COOH and —SH, or a hydrophobic functional group, such as —$C_6H_6$ or —$CH_3$.

According to another embodiment, the magnetic-cored dendrimer disclosed herein may be any one selected from the following Chemical Formulae (2) to (4):

(2)
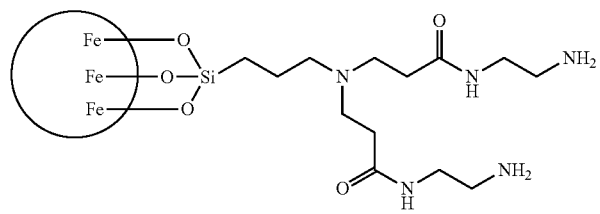

(3)
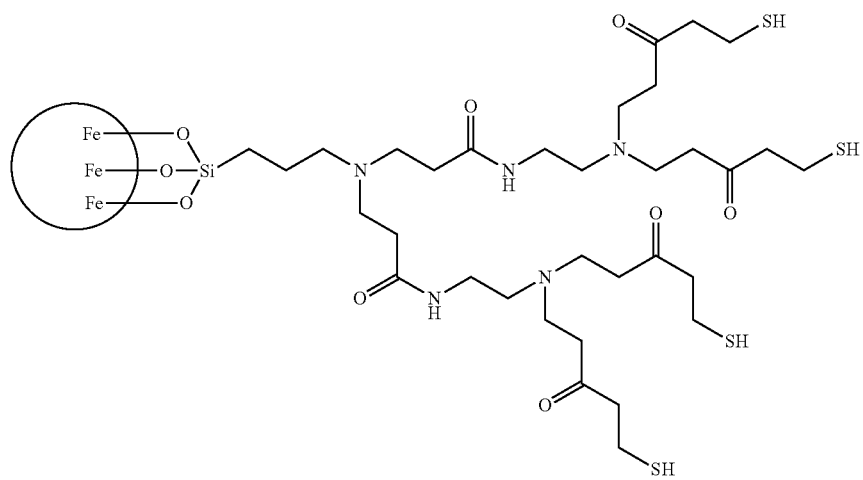

(4)
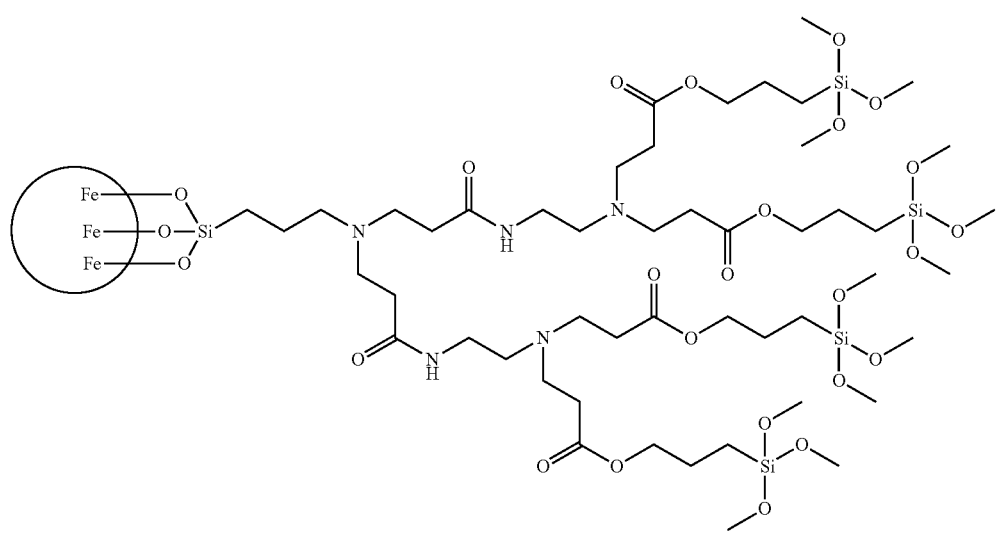

In another aspect, the method for separating hydrophilic or hydrophobic contaminants using the magnetic-cored dendrimer represented by the above Chemical Formula 1 includes: allowing the contaminants to be adsorbed on the magnetic-cored dendrimer; and separating the dendrimer having the contaminants adsorbed thereon by using a magnet.

In still another aspect, the apparatus for recovering magnetic nanoparticles includes: a wastewater tank 113 having a main body 113a to which wastewater containing magnetic nanoparticles is introduced, and a cover 113b disposed on the top of the main body; a plurality of magnetic bars 112 attached to the cover 113b to generate magnetic power; an adsorbent storage tank 136 from which magnetic fine powder capable of adsorbing the magnetic nanoparticles is supplied to the wastewater tank 113; and an agitator 115 provided in the wastewater tank to carry out agitation of the wastewater and the magnetic fine powder.

All materials exhibit a magnetic moment in a strong magnetic field, and thus they may be viewed as magnetic bodies in a strict sense. However, different materials have different directions and intensities magnetization in response to a given magnetic field. In addition, even a ferromagnetic material attracted to a magnet exhibits limited magnetic power in a system when it exists as fine particles. Thus, it is difficult to separate the particles using magnetic power without reinforcement of the magnetic properties of the particles.

Therefore, in the apparatus for recovering magnetic particles disclosed herein, magnetic fine powder is supplied from the adsorbent storage tank 136 to the wastewater tank 113. By doing so, cohesive force, such as van der Waals force or electrostatic attraction force, is applied to the magnetic nanoparticles floating on the wastewater, so that the magnetic nanoparticles may form magnetic floccules 120. Such magnetic floccules 120 are collected and separated by the magnetic force of the magnetic bar 112 having a magnetic force stronger than gravity or flow force during the agitation of the wastewater.

In the apparatus for recovering magnetic nanoparticles disclosed herein, the agitator 115 is used to mix the wastewater with the magnetic fine powder introduced to the wastewater tank 113, so that the magnetic particles present as the contaminants in the wastewater may be coupled well with the magnetic fine powder. During such mixing, the agitator 115 serves to assist the coupling between the magnetic fine powder and the magnetic nanoparticles and to maintain the magnetic floccules 120 at a uniform concentration in the wastewater. In this manner, the agitator serves to facilitate collection of the magnetic floccules 120 on the magnetic bar 112. Then, the wastewater, from which the magnetic floccules 120 are removed as mentioned above, is sent to an industrial water storage tank 148.

Unlike a general apparatus for recovering floating materials, which is provided with a water storage tank for agitation and another water storage tank for separation, the apparatus for recovering magnetic particles disclosed herein performs the agitation of wastewater and magnetic fine powder and the recovery of contaminants at the same time. Therefore, the process for purifying wastewater may be simplified and the processing time may be reduced. Further, the process may be carried out in a minimized space, and thus the apparatus may be located easily in a desired position.

Hereinafter, the apparatus for recovering magnetic nanoparticles will be explained with reference to the accompanying drawings.

Figure 10:
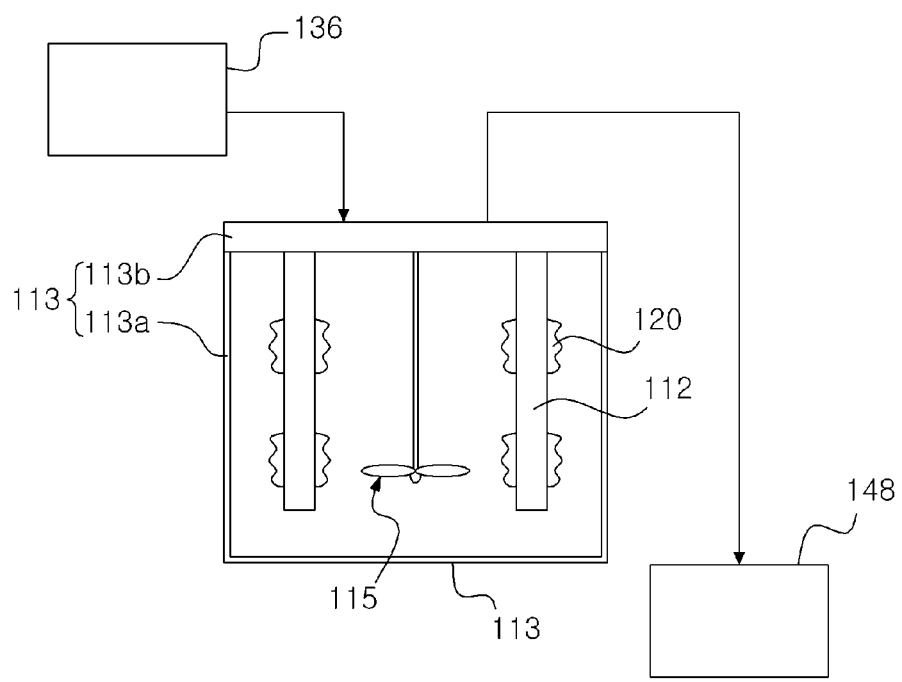
FIG. 10 is a schematic view showing the apparatus for recovering nanoparticles according to an exemplary embodiment.

FIG. 10 is a schematic view showing the apparatus for recovering magnetic nanoparticles according to an exemplary embodiment.

In the apparatus for recovering magnetic nanoparticles as shown in FIG. 10, wastewater is introduced first into the wastewater tank 113. Next, the magnetic fine powder contained in the adsorbent storage tank 136 is introduced into the wastewater tank 113, and the fine magnetic powder is allowed to be in more effective contact with the magnetic nanoparticles contained in the wastewater while they are mixed with each other by the agitator 115. This facilitates formation of the magnetic floccules 120. The magnetic floccules 120 formed by coupling between the fine magnetic powder and the magnetic nanoparticles substantially enhance the magnetic power of the magnetic nanoparticles. As a result, the magnetic nanoparticles may be collected on the magnetic bar 112 in the form of the magnetic floccules 120.

According to a particular embodiment, it is possible to facilitate formation of the magnetic floccules 120 as well as collection of the magnetic floccules 120 on the magnetic bar 112 by controlling the rotation speed of the agitator 115. In this context, the agitator may have a rotation speed of 100 rpm to 300 rpm. When the agitator 115 has a rotation speed less than 100 rpm, the number of effective contact between the magnetic fine powder and the magnetic nanoparticles is so small that the magnetic floccules 120 may not be formed in a sufficiently high rate. In this case, the number of magnetic floccules 120 that may be collected on the magnetic bar 112 per unit time is reduced. And, when the agitator 115 has a rotation speed greater than 300 rpm, the flow force of wastewater becomes larger than the magnetic force between the magnetic bar 112 and the magnetic floccules 120. Thus, the magnetic floccules sticking to the magnetic bar may be incorporated back to the wastewater, resulting in a drop in wastewater purification rate. Therefore, the agitator 115 in the apparatus for recovering magnetic nanoparticles disclosed herein is suitably maintained at a rotation speed of 100 rpm to 300 rpm.

Figure 11:
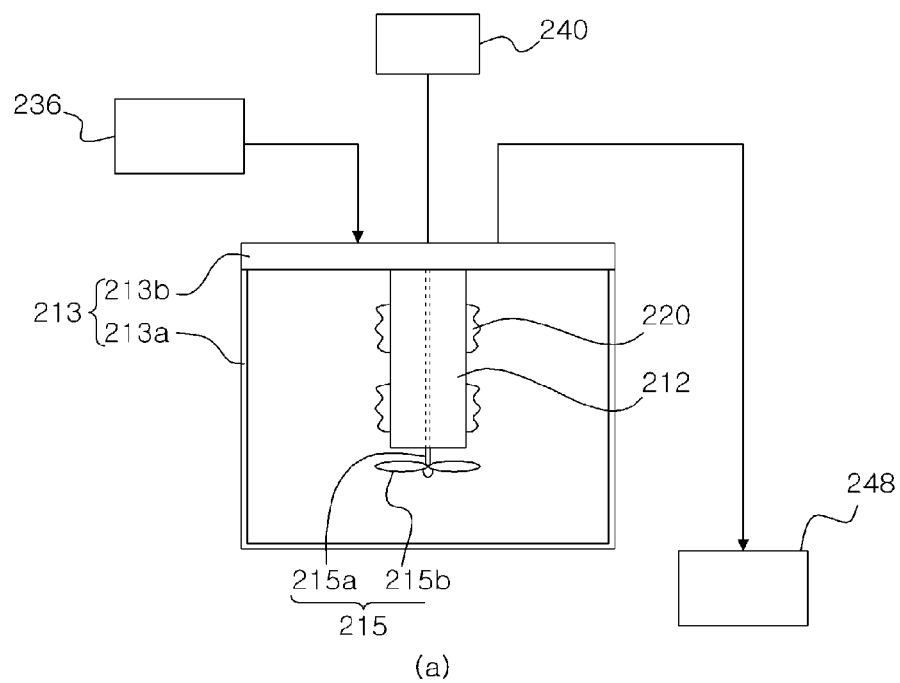
FIG. 11 shows schematic views of the apparatus for recovering magnetic nanoparticles according to some exemplary embodiments.
Figure 11:
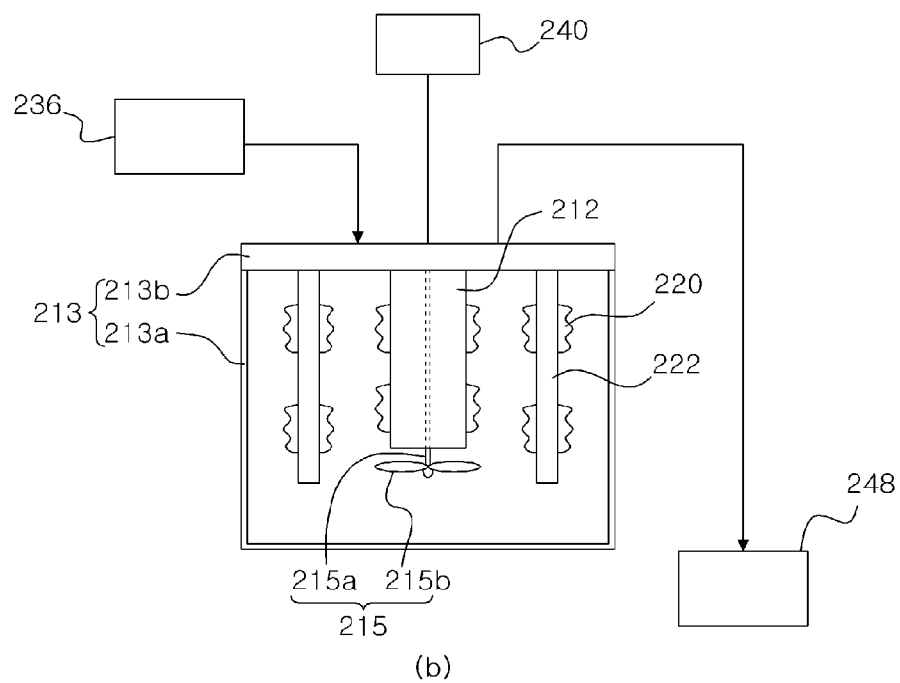

FIG. 11 shows schematic views of the apparatus for recovering magnetic nanoparticles according to some exemplary embodiments.

Although the apparatus for recovering magnetic nanoparticles may include the agitator 115 and the magnetic bar 112 collecting the magnetic floccules 120 separately from each other as shown in FIG. 10, the agitator 215 may be designed in such a manner that it is driven by the magnetic power of the magnetic bar 212, as shown in FIG. 11.

Referring to FIG. 11, the apparatus for recovering magnetic nanoparticles includes: a wastewater tank 213 having a main body 213a to which wastewater containing magnetic nanoparticles is introduced, and a cover 213b disposed on the top of the main body 213a; a hollow tubular magnetic bar 212 attached to the cover 213b to generate magnetic power; an adsorbent storage tank 236 from which magnetic fine powder capable of adsorbing the magnetic nanoparticles is supplied to the wastewater tank; and an agitator 215 penetrating through and disposed in the inner part of the magnetic bar 212, including a rotatable body 215a driven by the magnetic bar 212 and a propeller 215b attached to the end of the rotatable body 215a, and carrying out agitation of the wastewater and the magnetic fine powder.

In other words, the agitator 215 allows the rotatable body 215a disposed in the magnetic body 212 to be rotated, while electric energy is converted into kinetic energy in the presence of the magnetic field formed by the magnetic bar 212. Therefore, the propeller 215b attached to the end of the rotatable body 215a agitates the wastewater and the magnetic fine powder introduced into the wastewater tank 213.

Thus, in the apparatus for recovering magnetic nanoparticles according to an exemplary embodiment as shown in portion (a) of FIG. 11, the rotatable body 215a disposed in the hollow tubular magnetic bar 212 is rotated when a power is supplied, after the magnetic fine powder supplied from the adsorbent storage tank 236 and wastewater are introduced into the wastewater tank 213. When the magnetic fine powder is coupled with the magnetic nanoparticles to form the magnetic floccules 220, the magnetic floccules 220 are captured on the outer circumferential surface of the magnetic bar 212. Then, the industrial water treated through the above purification process for a predetermined time is sent to the industrial water tank 248. An outlet (not shown) through which the industrial water is discharged may be formed in the upper part of the wastewater tank 213. This is because non-separated contaminants may be precipitated on the bottom surface of the wastewater tank 213 due to their weights.

Any plural numbers of the hollow tubular magnetic bars 212 and the agitators 215 may be provided in the wastewater tank 213, as long as the flow of wastewater does not adversely affect collection of the magnetic floccules 220. Meanwhile, instead of multiple agitators 215, a plurality of magnetic bars 222 having a stick-like shape may be further provided in the wastewater tank 213, as shown in portion (b) of FIG. 11. The presence of such additional stick-like magnetic bars 222 increases the area used for collection of the magnetic floccules 220, thereby facilitating recovery of the magnetic floccules 220. Herein, the stick-like magnetic bars 222 and the magnetic bar 212 having the agitator 215 may be spaced from each other at regular intervals so that uniform magnetic force is applied between the magnetic bars 212, 222. In addition, to provide uniform flow of wastewater toward each of the stick-like magnetic bars 222, the magnetic bar 212 having the agitator 215 may be provided at the center of the wastewater tank 213. Particularly, the magnetic bars 112, 212, 222 may be an electromagnet or a permanent magnet. It is also possible to form the magnetic bars 112, 222 detachably, so that the number of magnetic bars 112, 222 provided in the wastewater tank 213 may be changed depending on the particular condition. When the magnetic bar 212 provided in the apparatus for recovering magnetic nanoparticles is selected as an electromagnet, the magnetic field shows intensities that may vary with the amount of electric current supplied thereto. Therefore, the rotatable body 215a disposed in the magnetic bar 212 may have different rotation speeds depending on the magnetic field intensities. Therefore, the apparatus for recovering magnetic nanoparticles according to an exemplary embodiment may further include a load control unit 240 controlling the speed of the rotatable body 215a so that the rotatable body 215a is maintained at a predetermined range of rotation speeds. More particularly, the load control unit 240 applies frictional force to the rotatable body 215a to limit the rotation speed thereof, when the magnetic field intensity increases to such a degree that the rotation speed of the rotatable body 215a exceeds a predetermined value, e.g., 300 rpm.

More particularly, the magnetic fine powder used in the apparatus for recovering magnetic nanoparticles disclosed herein may be the magnetic-cored dendrimer represented by the following Chemical Formula (1):

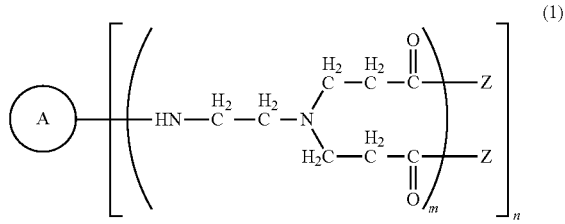

(1)

wherein A represents a metal nanoparticle; Z is a hydrophilic functional group or hydrophobic functional group; and m and n each represent an integer 1 or larger. Particularly, m may be an integer of 1 to 5.

According to a particular embodiment, the metal nanoparticle A may be an iron nanoparticle having a crystal form of magnetite ($Fe_3O_4$) or maghemite ($\gamma$-$Fe_2O_3$).

According to an embodiment, Z may be a hydrophilic functional group selected from the group consisting of —$NH_2$, —OH, —COOH and —SH, or a hydrophobic functional group, such as —$C_6H_6$ or —$CH_3$.

According to an embodiment, the magnetic-cored dendrimer may be any one selected from the above Chemical Formulae (2) to (4).

For example, the apparatus for recovering magnetic nanoparticles is useful for separating magnetic nanoparticles from industrial water of the iron making industry. Herein, the magnetic-cored dendrimer used as the magnetic fine powder permits separation of hydrophilic or hydrophobic contaminants as well as the magnetic nanoparticles. In the same manner as the formation of the magnetic nanoparticles into the magnetic floccules 220, the hydrophilic or hydrophobic contaminants may be adsorbed on the magnetic-cored dendrimer, and then the dendrimer having the contaminants adsorbed thereon may be separated out by the magnetic bar 212. In other words, the apparatus may be applied to separate various contaminants from various types of industrial water in addition to industrial water of the iron making industry.

EXAMPLES

The examples and experiments will now be described. The following examples and experiments are for illustrative purposes only and not intended to limit the scope of this disclosure.

Example 1

Preparation of Magnetic-Cored Dendrimer

Magnetite nanoparticles (MNP) are prepared by co-precipitation. First, a solution containing mixed $Fe^{2+}$ and $Fe^{3+}$ ions ($Fe^{2+}/Fe^{2+}$=2) is introduced into 4 M NaOH solution to perform co-precipitation. The resultant solution is rinsed with water and methanol several times and MNP is separated by using a magnet.

The resultant MNP is dispersed in ethanol, and 3-aminopropyltrimethoxysilane [$NH_2(CH_2)_3Si(OCH_3)_3$, APTS] is added thereto to form an MNP dendrimer (G=0). Then, an excessive amount of methyl acrylate ($C_4H_6O_2$) and ethylene diamine ($C_2H_8N_2$, EDA) are added thereto alternately to obtain a second-generation MNP PAMAM dendrimer (MNP-D (G=2)). For the preparation of the second-generation, rinsing is carried out with distilled water and methanol. Next, a sonicator is used to perform ultrasonic dispersion for 10 minutes for the purpose of dispersion of the magnetic-cored dendrimer. The magnetic-cored dendrimer is stored in a vacuum desiccator to prevent exposure to outside. A rotary evaporator (Hanshin Co.) is used throughout the preparation in this example, and preparation of each generation is maintained for 24 hours. FIG. 1 is a schematic view showing the preparation of a magnetic-cored dendrimer end-capped with $NH_2$ groups.

Figure 2:
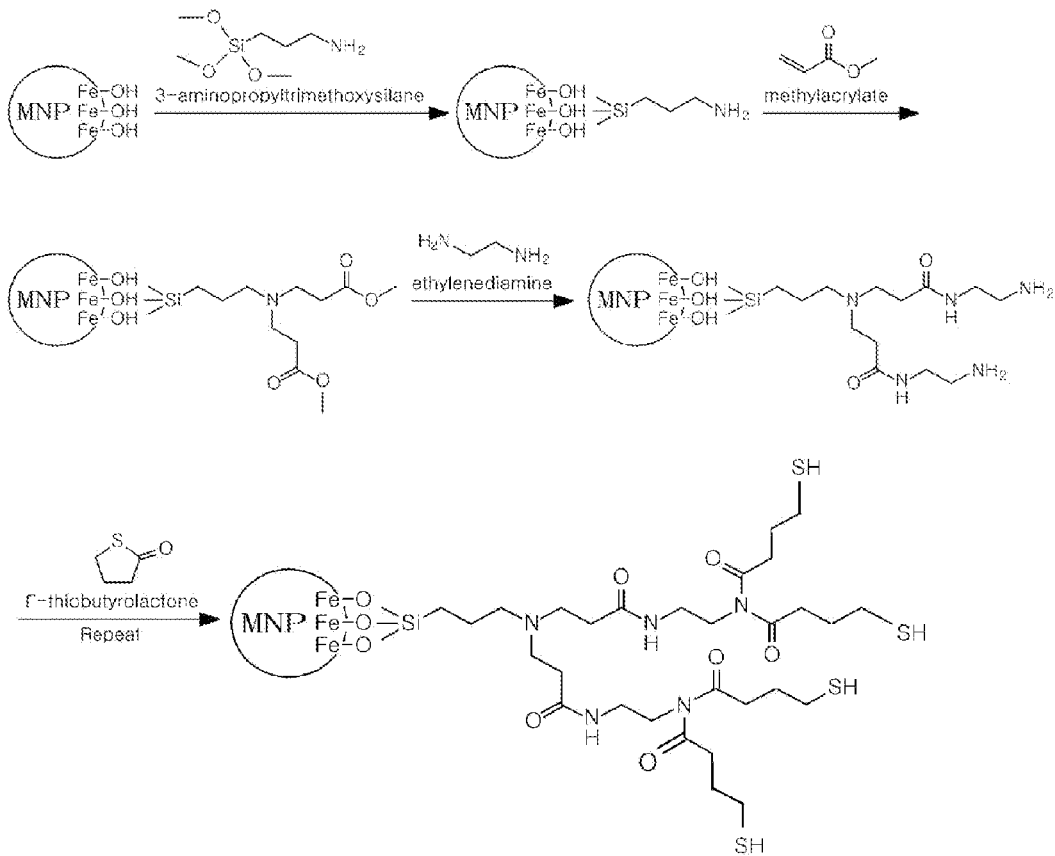
FIG. 2 is a schematic view showing the preparation of a magnetic-cored dendrimer end-capped with SH groups.

When an excessive amount of gamma $\gamma$-thiobutyrolactone is added during the preparation of the dendrimer, the resultant dendrimer has terminal SH groups. FIG. 2 is a schematic view showing the preparation of a magnetic-cored dendrimer end-capped with SH groups.

Figure 3:
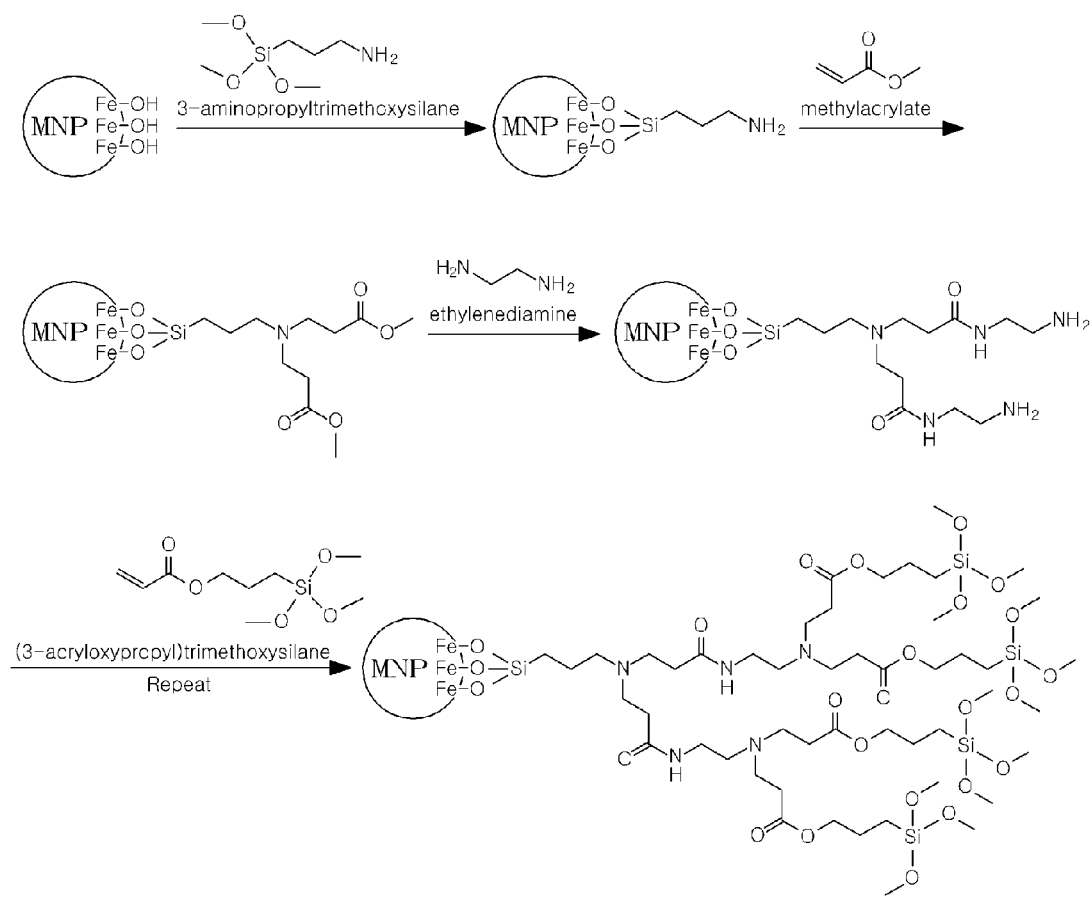
FIG. 3 is a schematic view showing the preparation of a magnetic-cored dendrimer end-capped with $CH_3$ groups.

When an excessive amount of (3-acryloxypropyl)trimethoxysilane is added during the preparation of the dendrimer, the resultant dendrimer has terminal $CH_3$ groups. The dendrimer end-capped with $CH_3$ groups has a hydrophobic surface. Thus, it is expected that such a dendrimer is useful for adsorption of hydrophobic organic contaminants. FIG. 3 is a schematic view showing the preparation of a magnetic-cored dendrimer end-capped with $CH_3$ groups.

Test Example 1

Analysis of Magnetite Nanoparticles (MNP)

Figure 4:
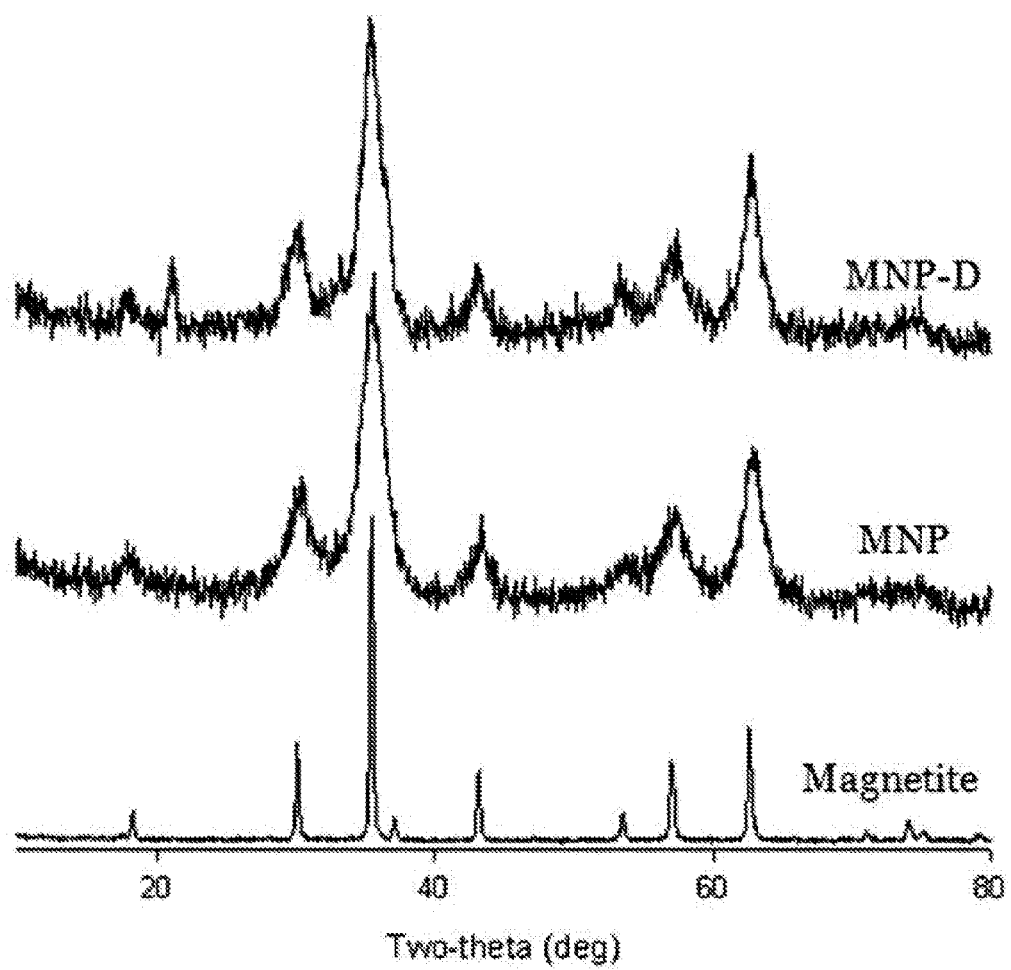
FIG. 4 shows the results of XRD analysis of MNP as a core of a dendrimer.

To characterize the synthetic MNP obtained herein, X-ray diffractometry (XRD) is carried out. FIG. 4 shows the result of XRD analysis of MNP as a core of dendrimer.

It is shown from XRD that the synthetic MNP has peaks at the same positions as magnetite ($Fe_3O_4$) available from Sigma Co. This demonstrates that the synthetic MNP is magnetite. Referring to FIG. 4, some peaks that are found in MNP-D appear in MNP-D. This suggests that the properties of synthetic magnetite are not significantly affected by the synthetic procedure.

Figure 5:
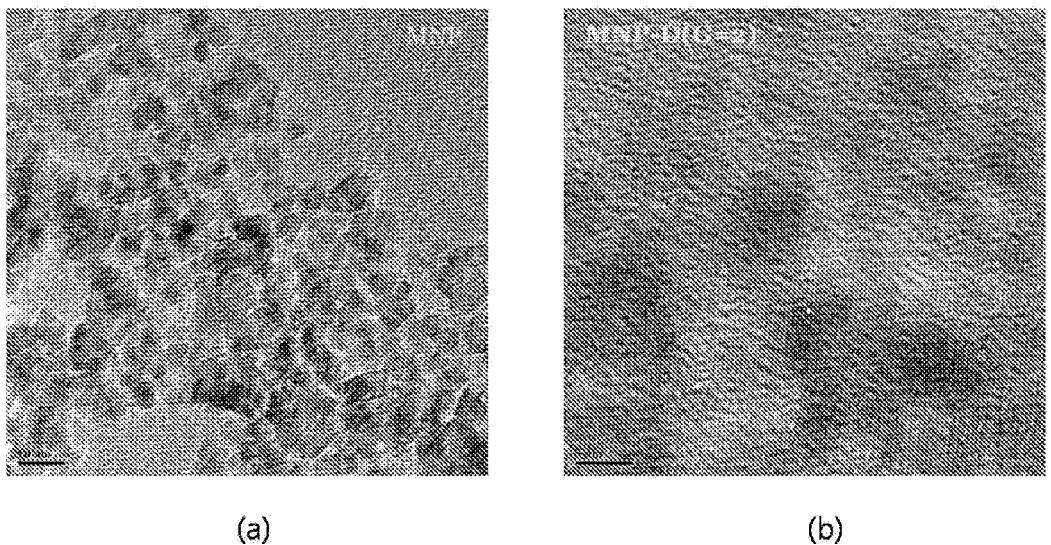
FIG. 5 shows HR-TEM images of MNP (portion (a)) and MNP-D (G=2) (portion (b)) prepared from iron oxide.

FIG. 5 shows HR-TEM images of iron oxide available from Sigma Co., and MNP (portion (a)) and MNP-D (G=2) (portion (b)) prepared from iron oxide. After the particle size of each sample is measured and averaged, it is shown that the iron oxide has a particle size of about 50 nm, while MNP and MNP-D (G=2) have a particle size of about 5 nm and about 6 nm, respectively.

Figure 6:
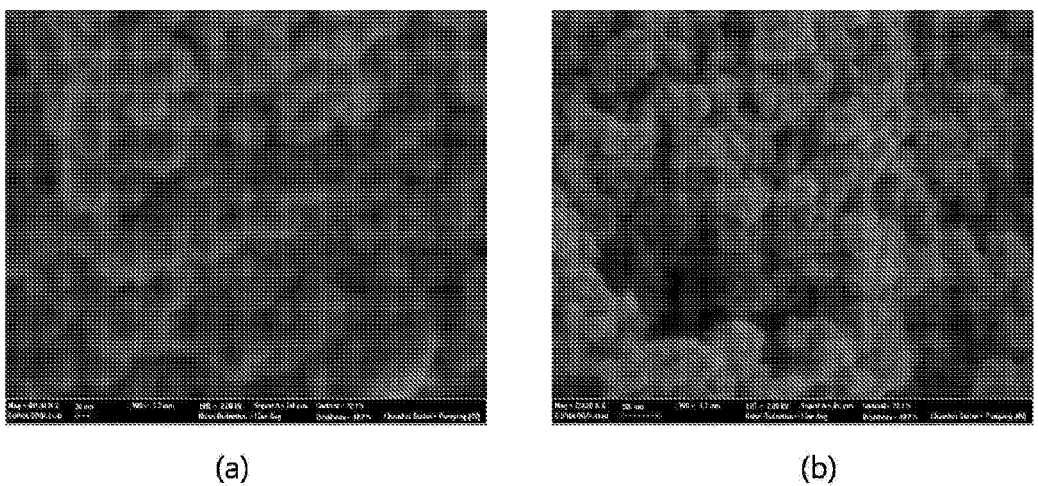
FIG. 6 shows FE-SEM images of a magnetic-cored dendrimer.

FIG. 6 shows FE-SEM images of a magnetic-cored dendrimer. It can be seen that the dendrimer maintains its shape agglomerated by magnetic property and has a particle size of 5 to 10 nm.

Figure 7:
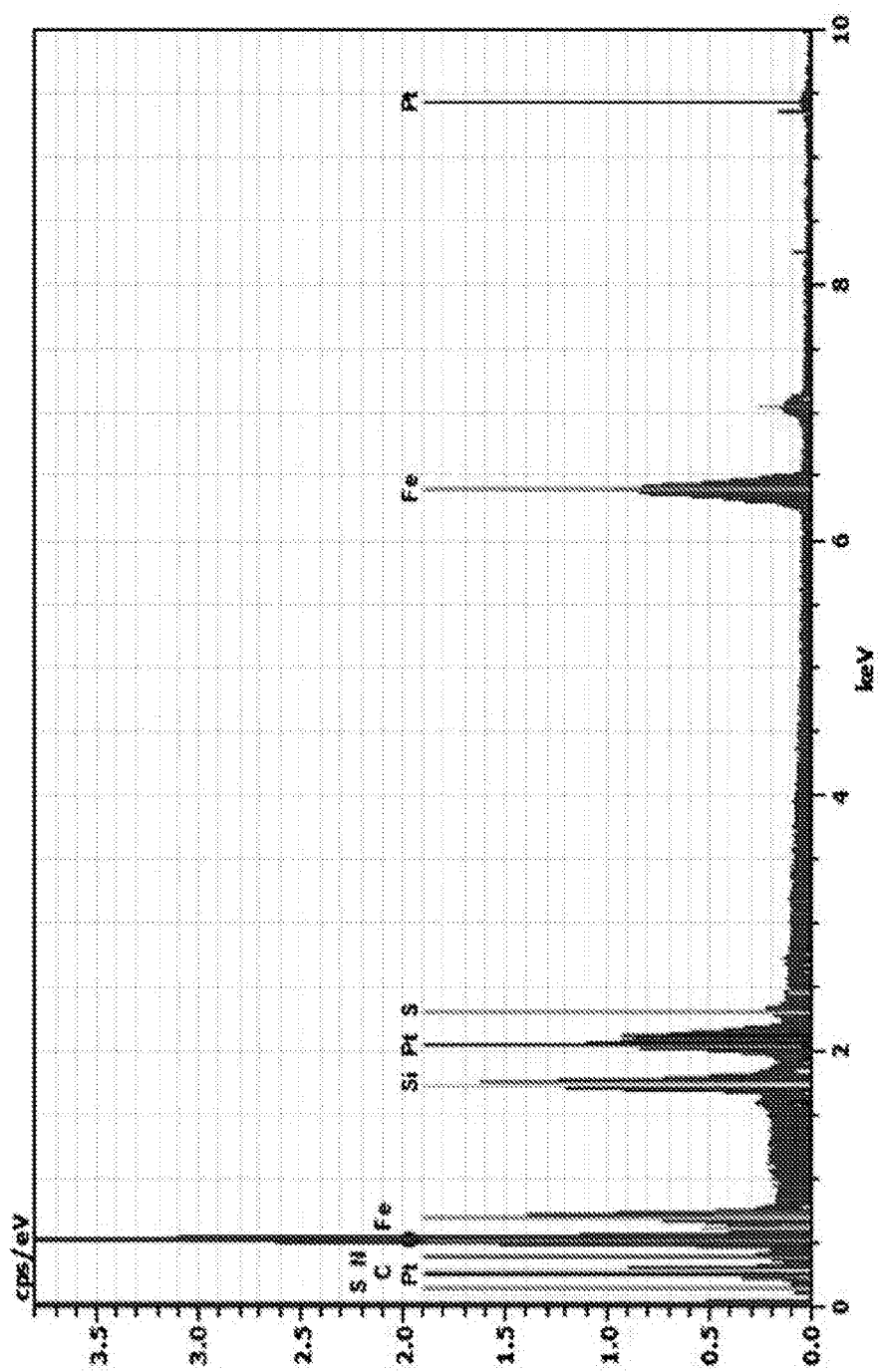
FIGS. 7 and 8 show the results of energy-dispersive X-ray spectroscopy (EDS) of the magnetic-cored dendrimers end-capped with SH and $CH_3$ groups.
Figure 8:
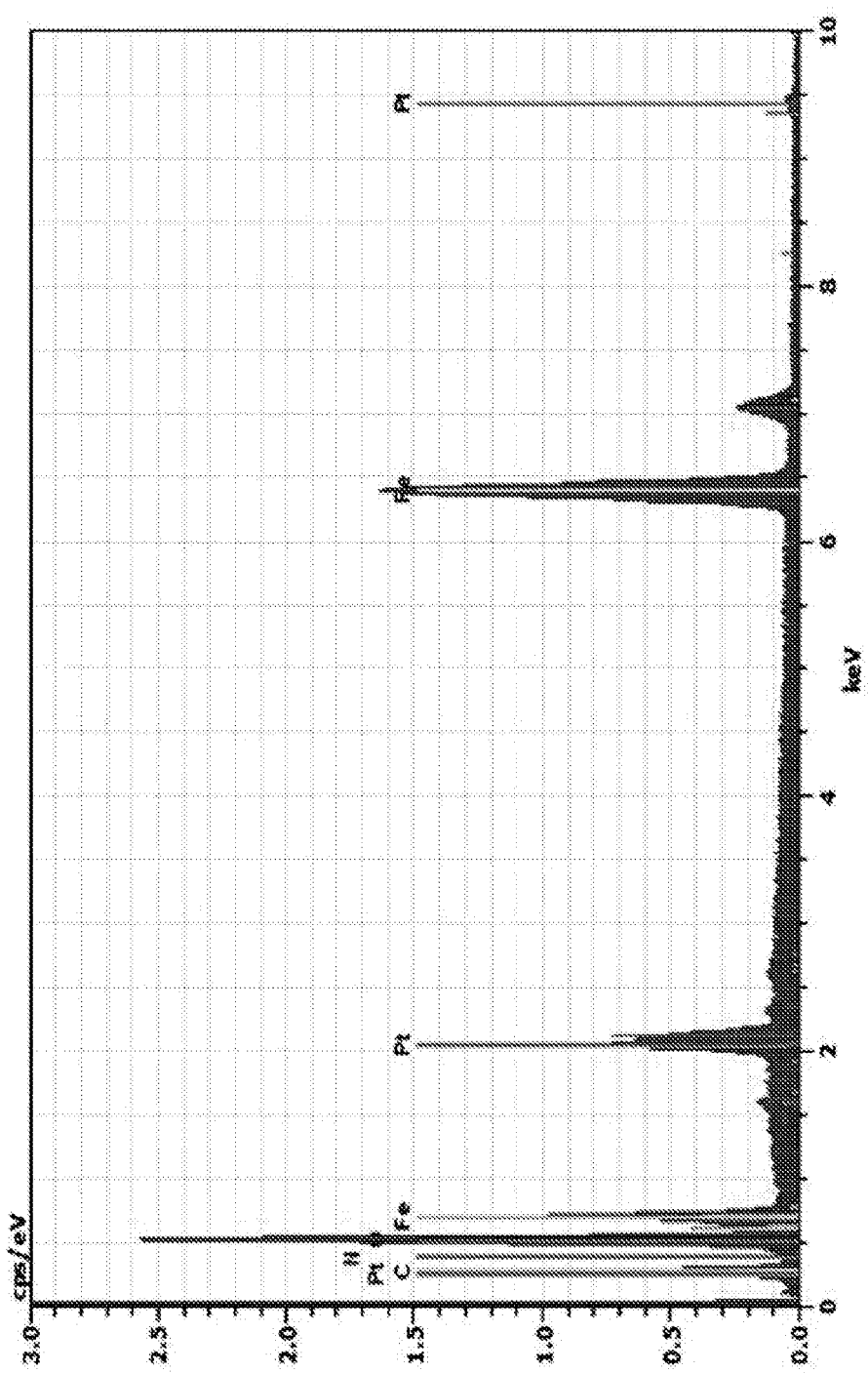

FIGS. 7 and 8 show the results of energy-dispersive X-ray spectroscopy (EDS) of a magnetic-cored dendrimer end-capped with SH or $CH_3$ groups. As determined from the presence of S and C peaks in the resultant dendrimer, the dendrimer is shown to have terminal SH and $CH_3$ groups.

Test Example 2

Removal of Cadmium

Figure 9B:
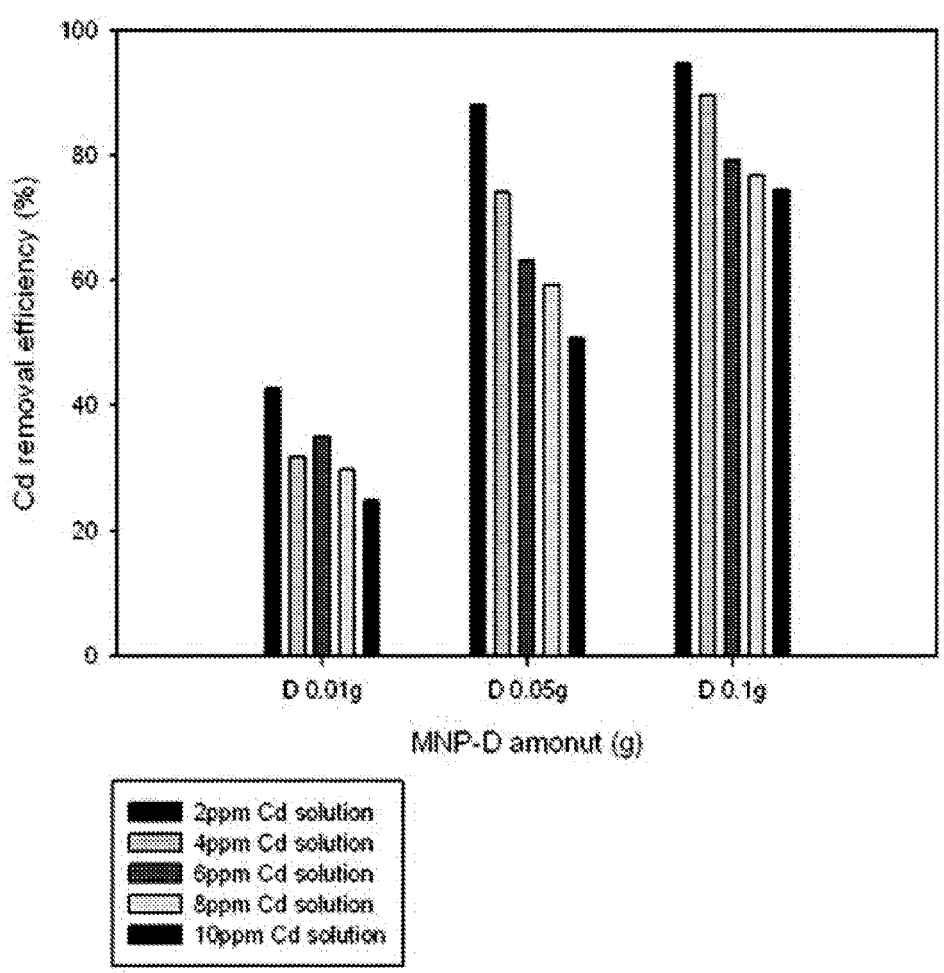
Figure 9C:
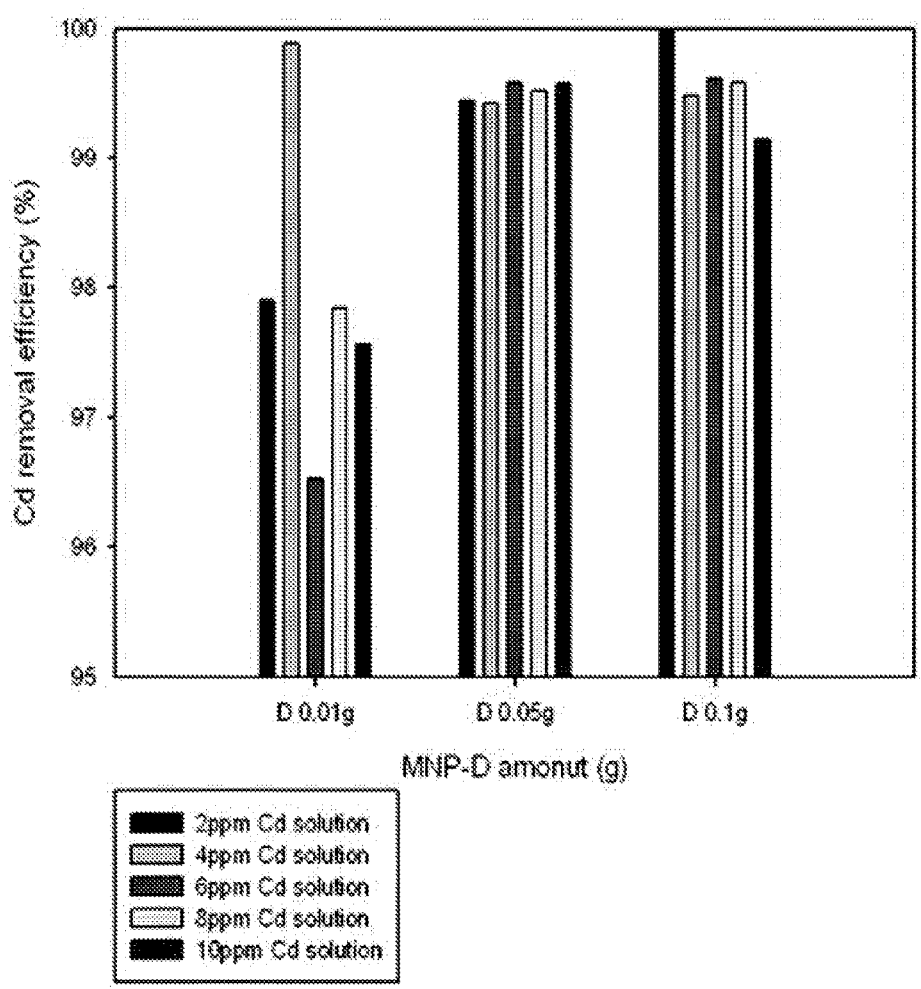

A series of dilutions with a concentration of 0.1, 0.5, 1. 1.5, 2 and 3 ppm is prepared from 100 ppm cadmium solution and a standard curve is plotted. Several dilutions of cadmium solution, each having a concentration of 2, 4, 6, 8 and 10 ppm, are prepared for the test. Then, 30 mL of each dilution is introduced into a 40 mL vial after adjusting the pH to 3, 6 or 11, and the magnetic-cored dendrimer ($NH_2$-terminal) (G=2) is further introduced thereto in an amount of 0.01 g, 0.05 g or 0.1 g. The resultant mixture is agitated sufficiently with vortex, and the concentration of cadmium is determined by atomic absorption spectrometry (AAS). The cadmium removal test is carried out after adjusting the final pH to 3, 6 or 11. The results are shown in FIGS. 9A to 9C.

When pH is 11, all tests provide a removal ratio of 96% or higher, suggesting that substantially all cadmium is removed. On the other hand, when pH is 3, cadmium is not removed substantially. Therefore, it can be seen from the above results that since cadmium adsorbed on MNP-D (G=2) is desorbed substantially at low pH, used MNP-D (G=2) may be reutilized. This demonstrates that the magnetic-cored dendrimer is an effective adsorbent for cadmium, because it allows adsorption of cadmium at high pH and desorption of cadmium at low pH. In addition, since the magnetic-cored dendrimer has a nano-scale size, unlike other adsorbents, it has a significantly high specific surface area. Further, since the dendrimer has a magnetite core, it may be recovered effectively and efficiently through the use of a magnet.

Test Example 3

Apparatus for Recovering Magnetic Nanoparticles

Figure 12:
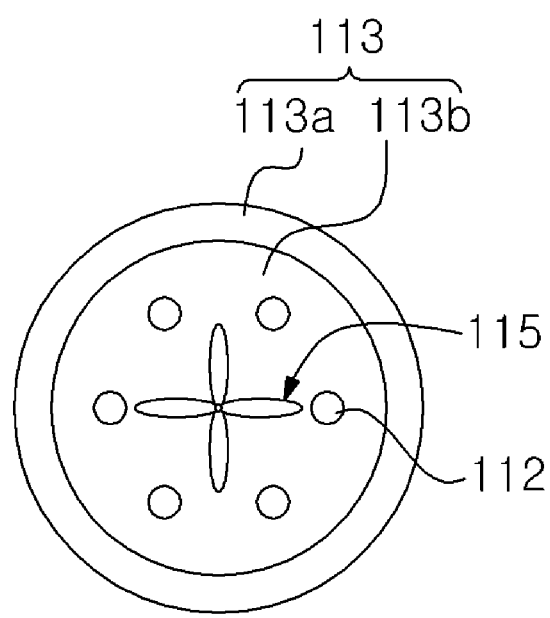
FIG. 12 is a bottom view of the wastewater tank according to an exemplary embodiment.

As shown in FIG. 10, six magnetic bars 112 having a diameter of 22 mm and a height of 100 mm are provided in a wastewater tank 113 having an inner diameter of 130 mm and a height of 150 mm. The wastewater tank has a main body 113a made of stainless steel and a cover 113b made of acetal. The wastewater tank 113 is further provided with an agitator 115 provided at the center of the inner part of the wastewater tank 113. FIG. 12 is a bottom view of the wastewater tank 113, wherein the bottom surface of the wastewater tank 113 is omitted to provide a simple and clear understanding of the inner part thereof.

Figure 13:
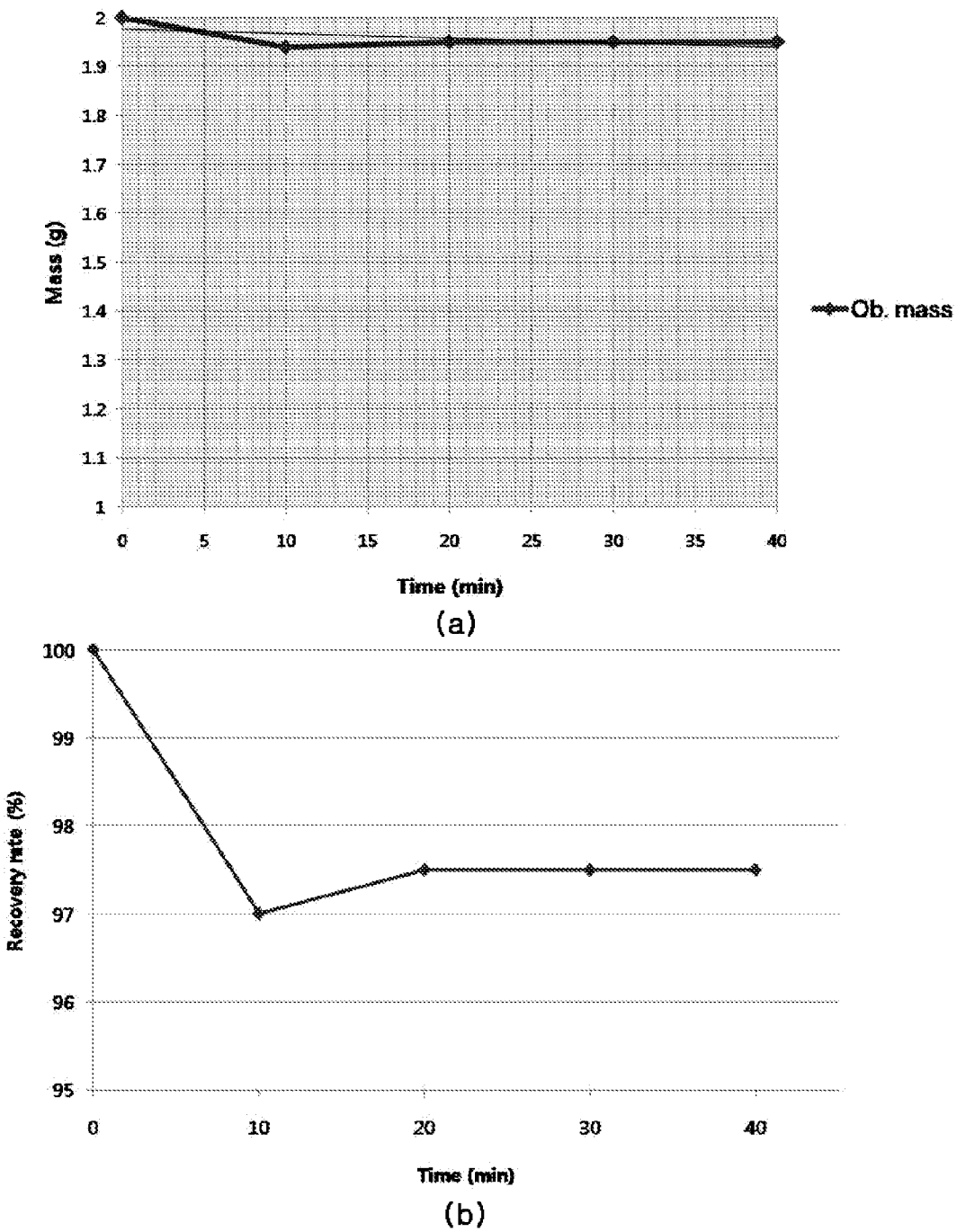
FIG. 13 shows graphs illustrating the test results of the apparatus for recovering magnetic nanoparticles according to an exemplary embodiment.

To measure the recovery rate after the agitation of the magnetic nanoparticles and the magnetic-cored dendrimer, each sample to be tested is weighed after drying. Each sample is dispersed in triple distilled water prepared in a 500 mL beaker. Then, the beaker content is poured completely into the apparatus as described above, agitated therein while the magnetic bars 112 in the absence of magnetic field, and then a magnetic field is applied at an interval of 10 minutes. After that, each sample is recovered. The sample is dried and weighed. The tested sample is 2 g of iron (Fe) having a particle size of 0.1 μm and the agitator is driven under 200 rpm. FIG. 8 shows the result obtained after recovering the magnetic nanoparticles. The magnetic nanoparticles are recovered after 2 g of the initial magnetic nanoparticles are agitated in the wastewater tank 113 and a magnetic field is applied thereto. Herein, portion (a) and portion (b) of FIG. 13 show the amount and ratio of the recovered magnetic nanoparticles. It is shown that the recovery is substantially completed in 20 minutes after the application of magnetic field, and the final recovery rate is 97%. In addition, considering experimental errors occurring during drying and sample transfer, it seems that the actual non-recovered proportion is lower than 3%.

Figure 14:
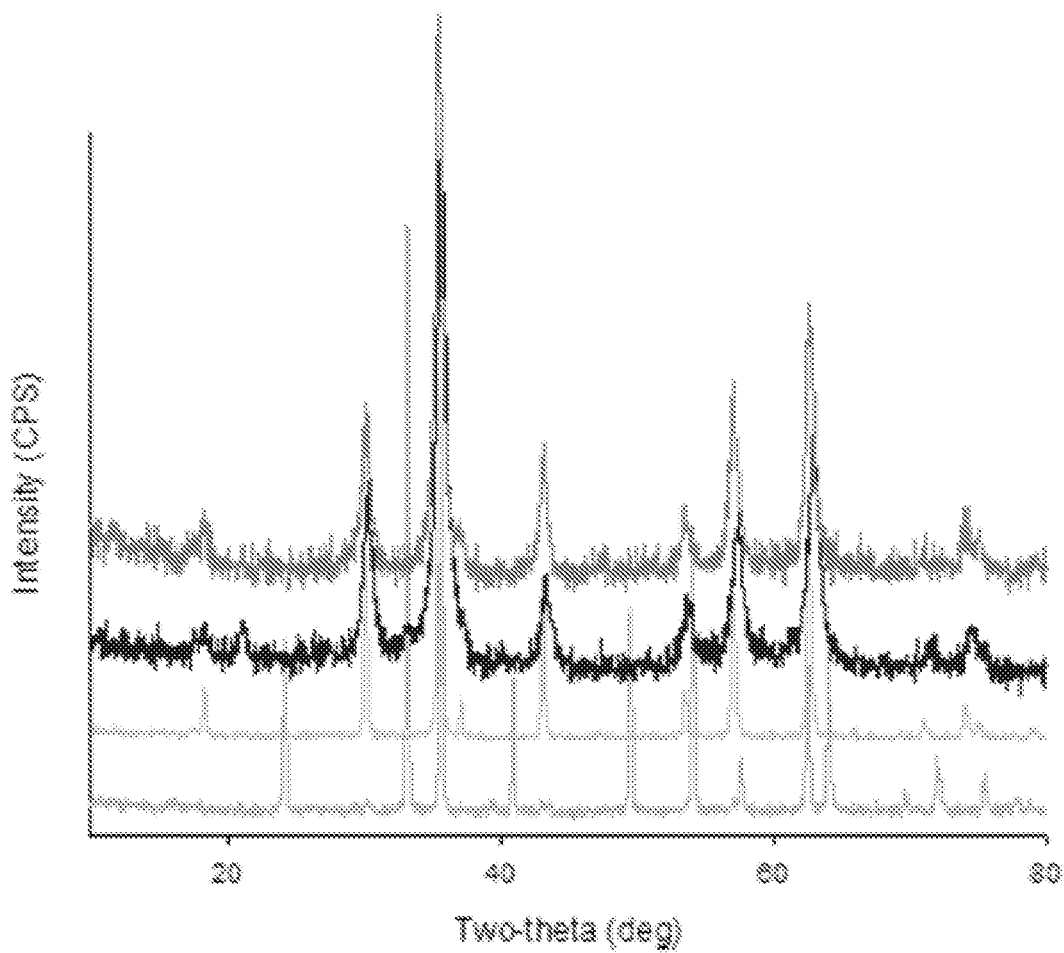
FIG. 14 is a graph showing the results of preparation of MNP and MD (G=1)
Figure 15A:
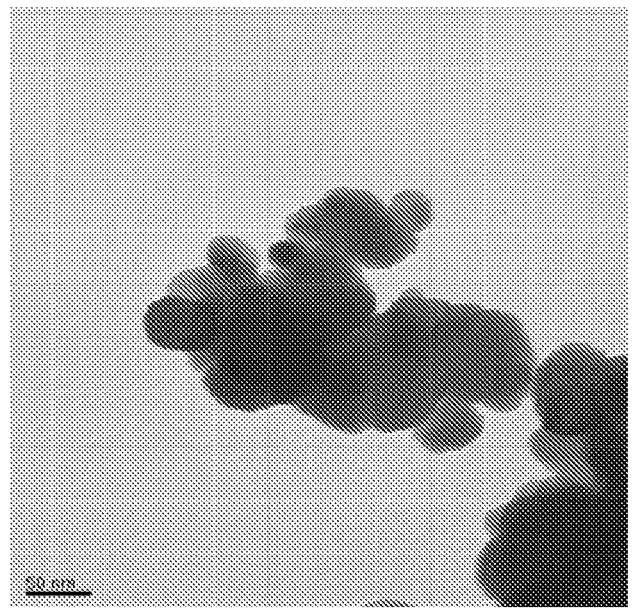
FIG. 15A shows magnetite with a size of 40 nm to 50 nm available from Sigma Co.
Figure 15B:
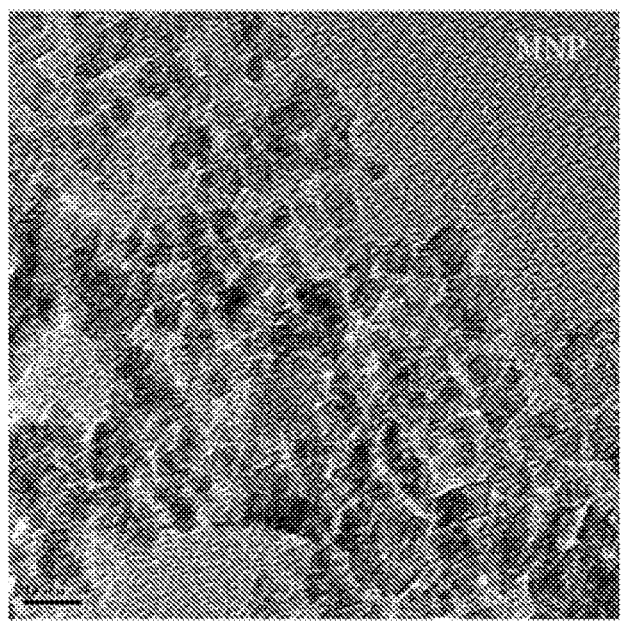
FIG. 15B shows synthetic MNP with a size of 4 nm to 5 nm.
Figure 15C:
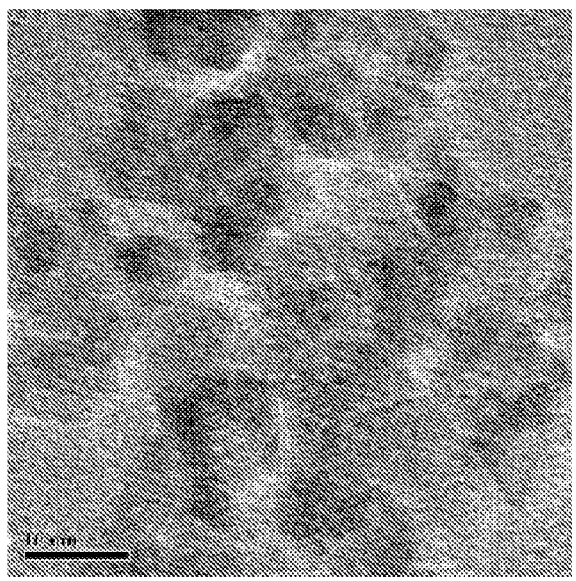
FIG. 15C shows synthetic MD (G=1) with a size of 6 nm-7 nm.
Figure 16:
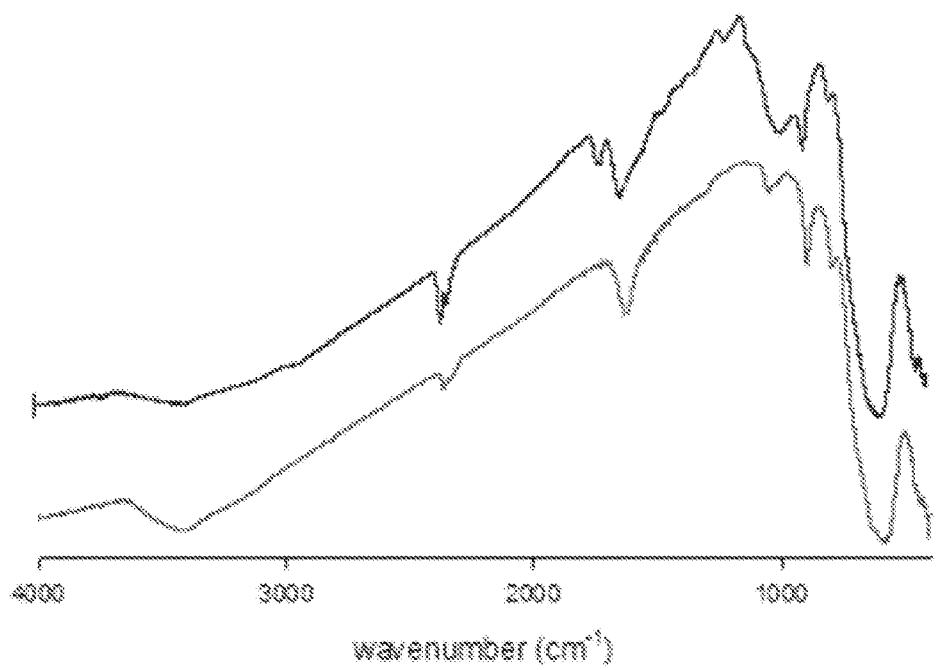
FIG. 16 is a graph showing the results of preparation of MNP and MD (G=1)
Figure 17A:
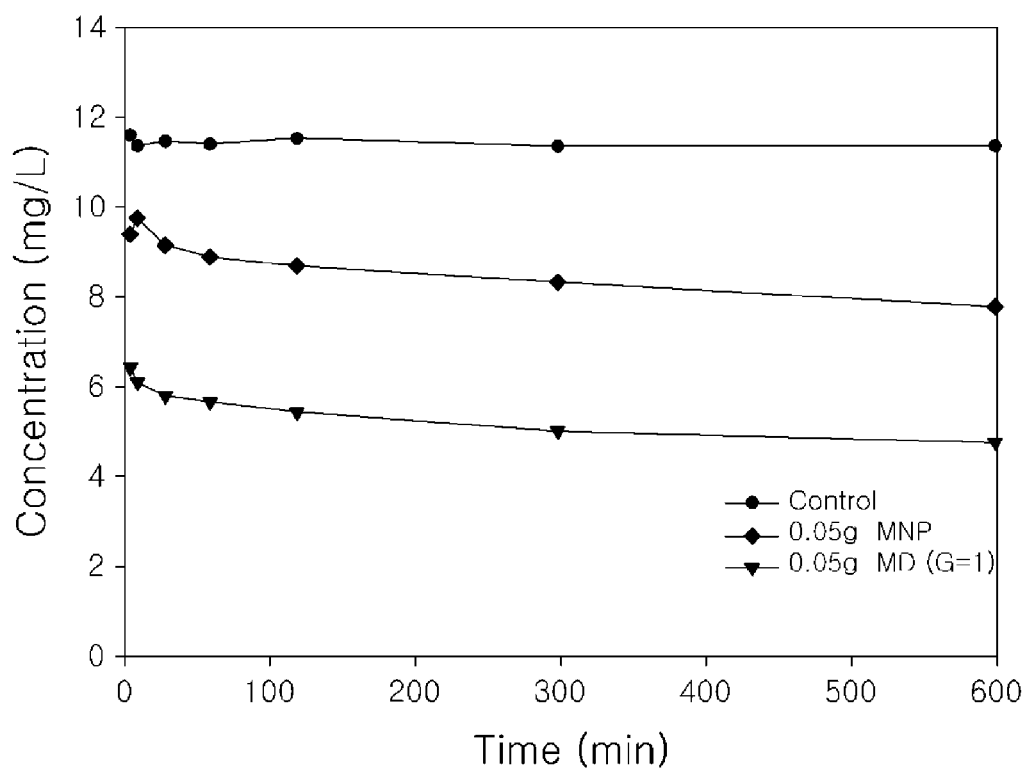
FIGS. 17A and 17B are graphs showing the results of the nickel removal test according to another exemplary embodiment.
Figure 17B:
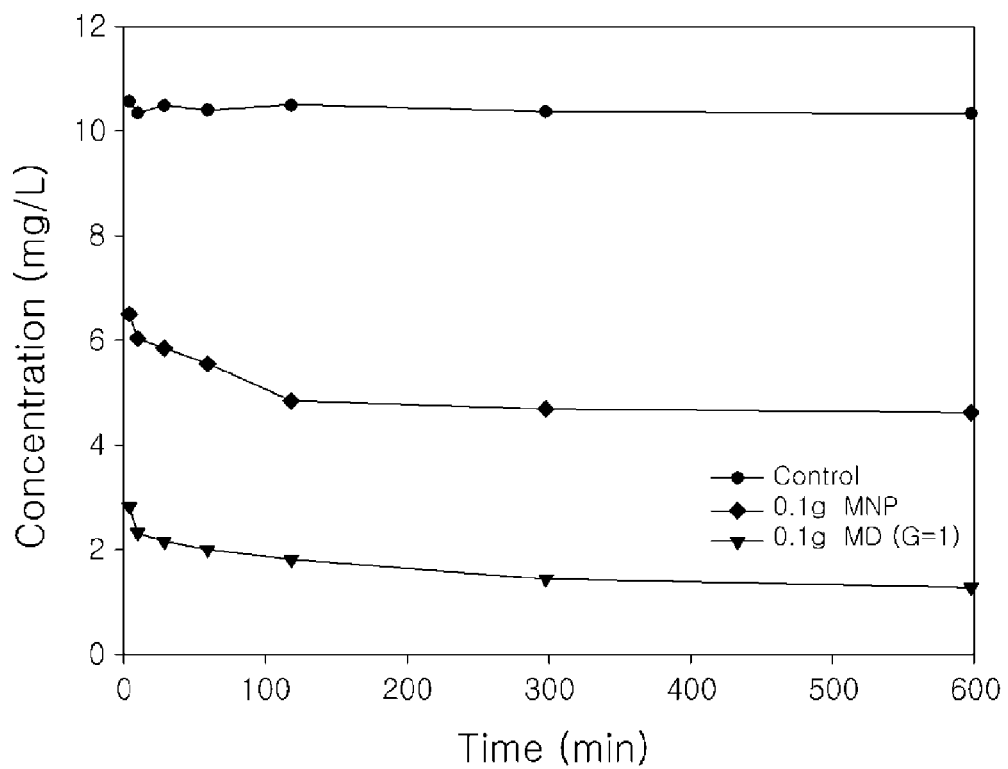
Figure 18A:
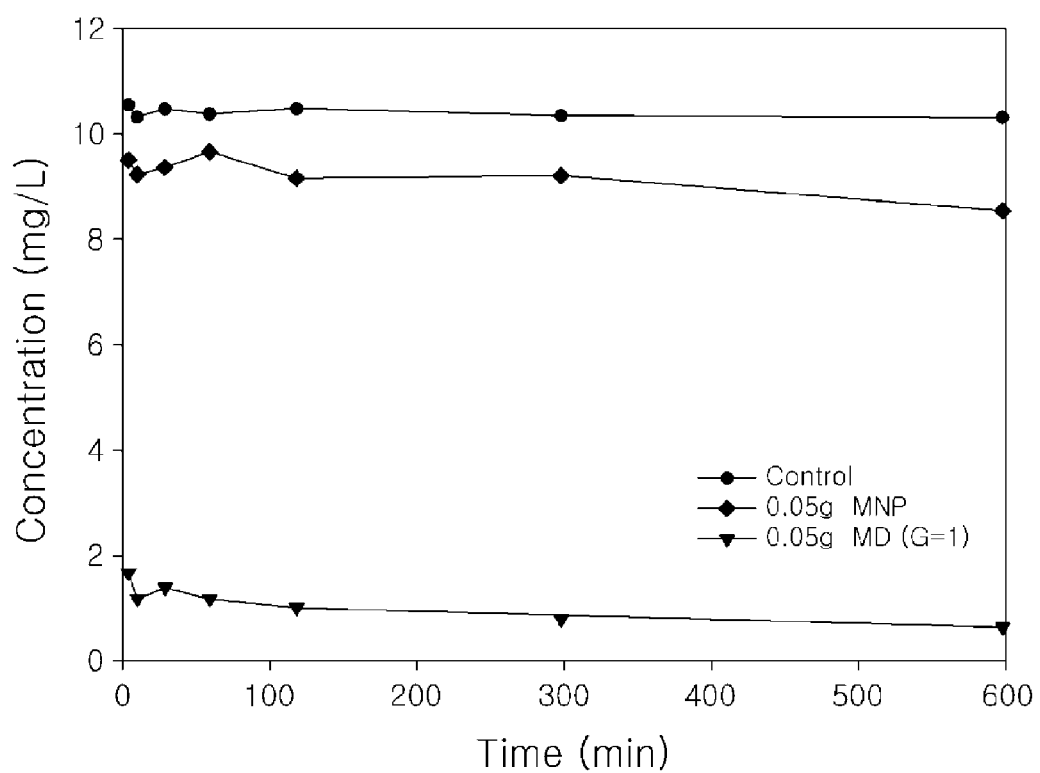
FIGS. 18A and 18B are graphs showing the results of the cadmium removal test according to another exemplary embodiment.
Figure 18B:
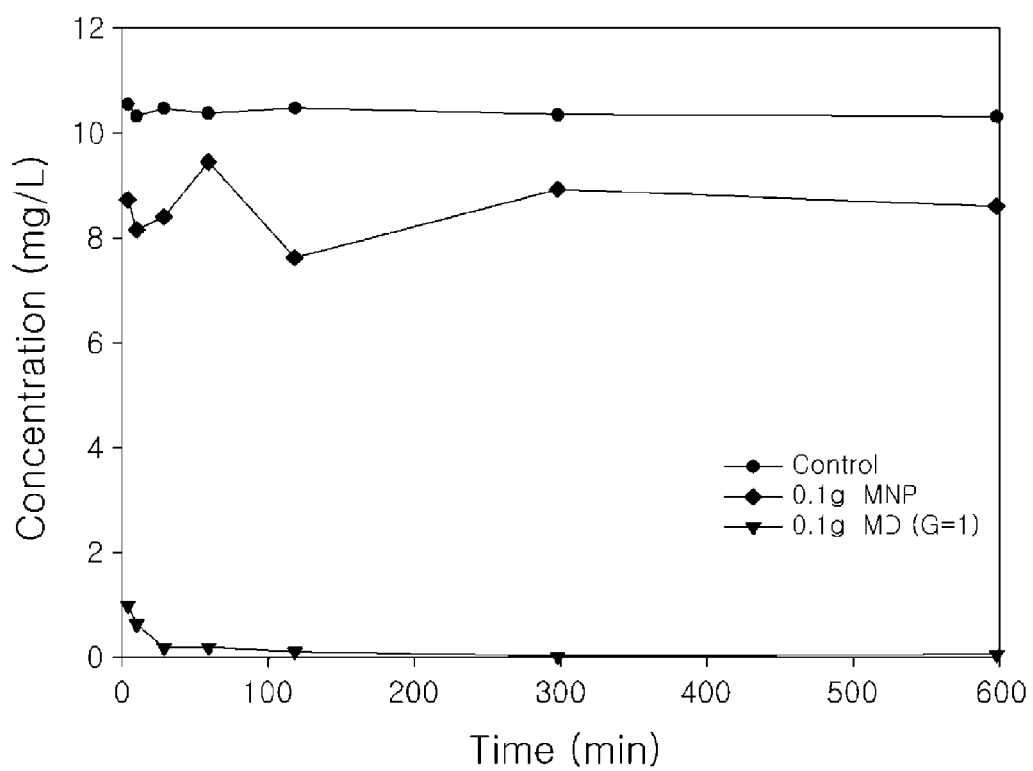
Figure 19A:
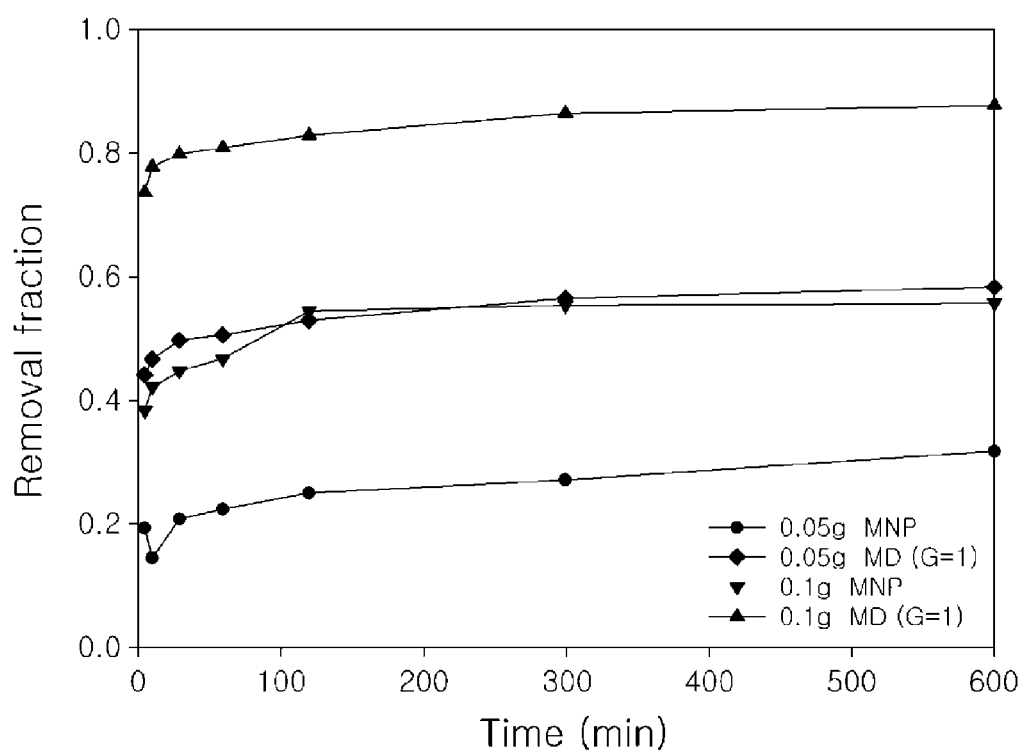
FIGS. 19A and 19B are graphs showing the results of the nickel and cadmium removal test according to another exemplary embodiment.
Figure 19B:
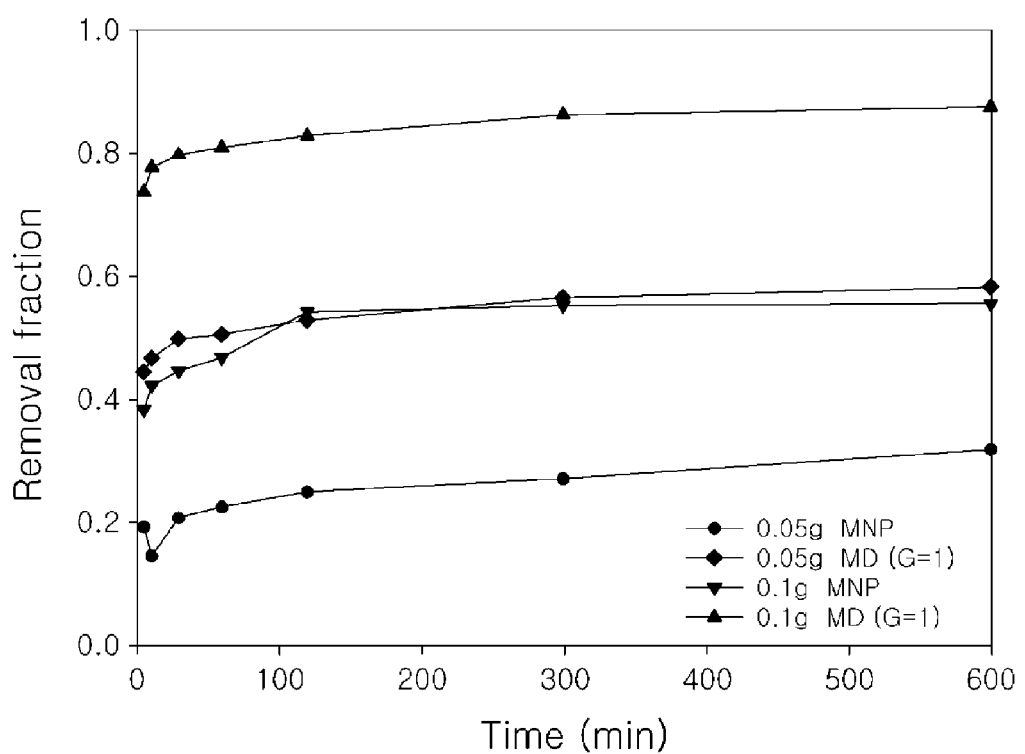
Figure 20A:
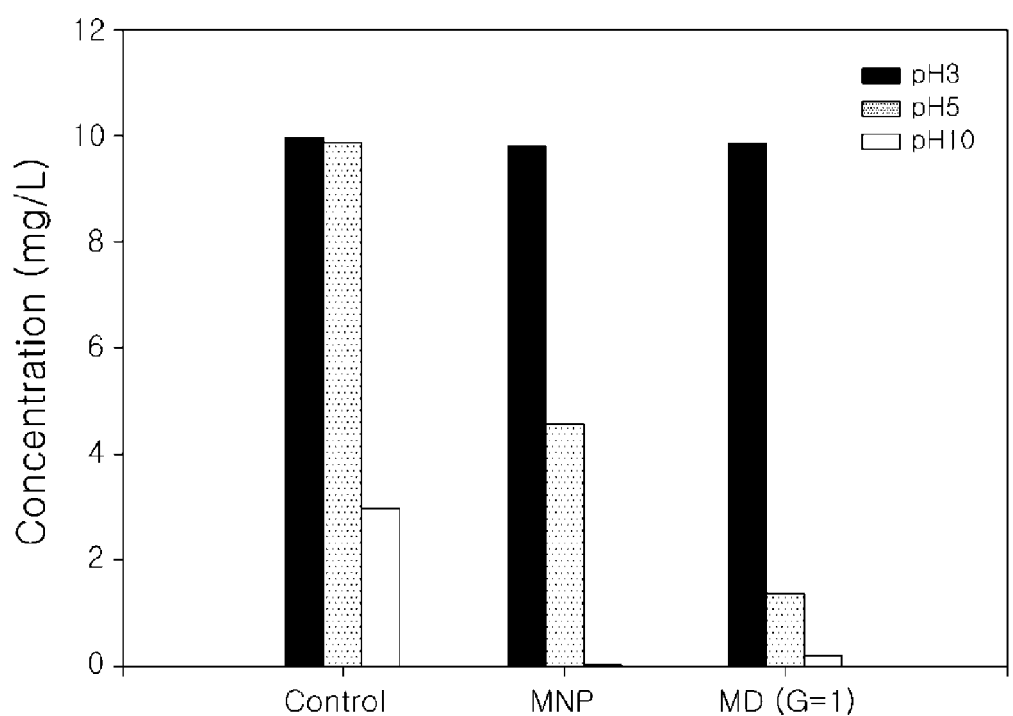
FIGS. 20A to 20C are graphs showing the results of the nickel and cadmium removal test according to another exemplary embodiment.
Figure 20B:
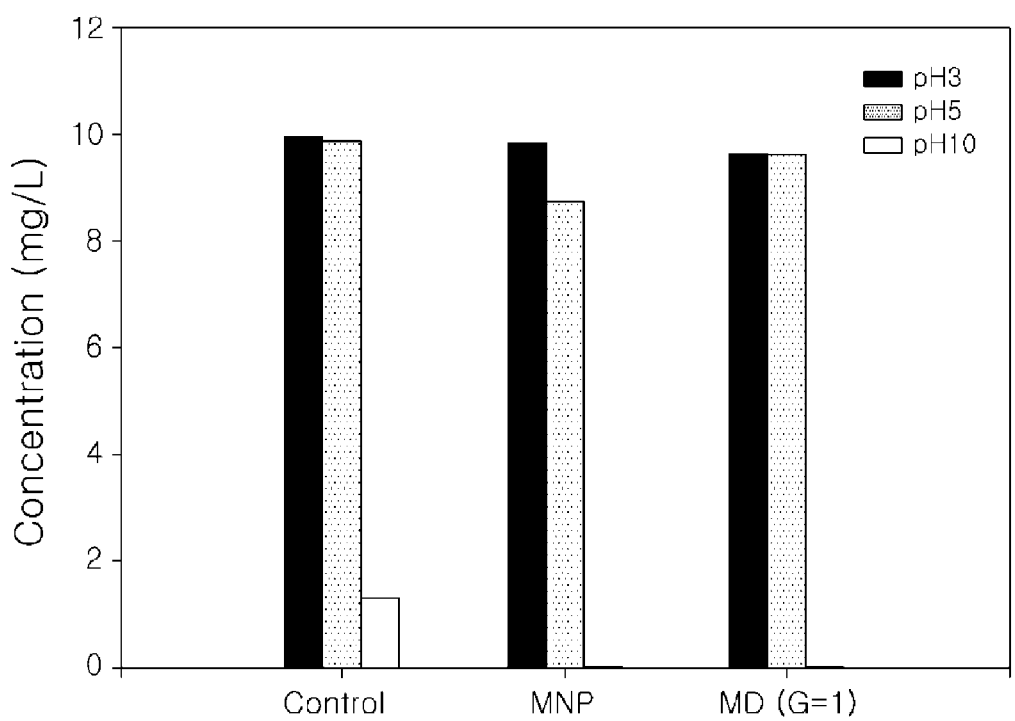
Figure 20C:
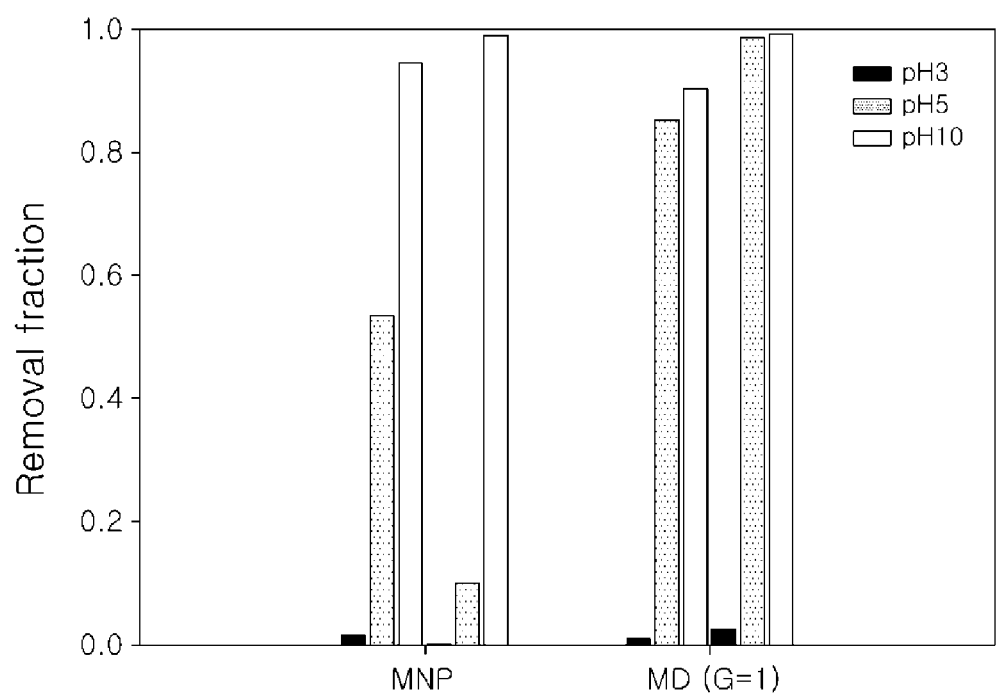

FIG. 14 is a graph showing the results of preparation of MNP and MD (G=1). FIGS. 15A to 15C show magnetite with a size of 40 nm to 50 nm available from Sigma Co. and synthetic MNP and MD (G=1) corresponding to each particle size. FIG. 16 is a graph showing the results of preparation of MNP and MD (G=1). FIGS. 17A to 20 are graphs showing the results of the nickel and cadmium removal test. It can be seen from these test results that the apparatus for recovering magnetic nanoparticles using the dendrimer obtained from Example 1 as magnetic fine powder provides an excellent effect of removing heavy metals.

While the present disclosure has been described with respect to the specific embodiments, it will be apparent to those skilled in the art that various changes and modifications may be made without departing from the spirit and scope of the disclosure as defined in the following claims.

What is claimed is:

1. A magnetic-cored dendrimer represented by the following Chemical Formula (1) or (2):

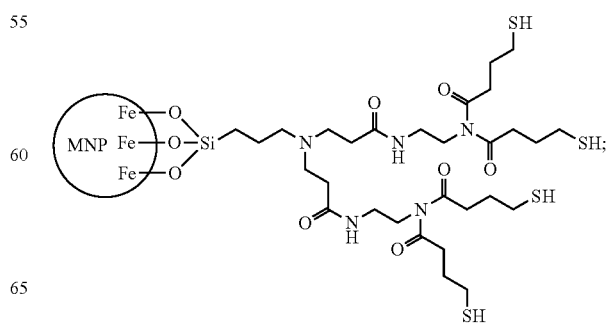

(1)

(2)
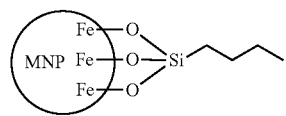
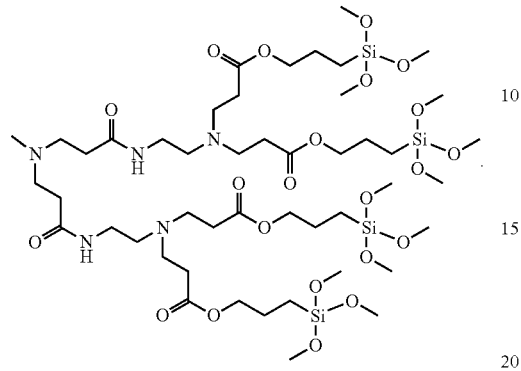
* * * * *